United States Patent
Konstandopoulos

(10) Patent No.: US 7,891,176 B2
(45) Date of Patent: *Feb. 22, 2011

(54) EXHAUST GAS PURIFYING APPARATUS

(75) Inventor: Athanasios G. Konstandopoulos, 45 Tselepi Street, Thessaloniki (GR) 54352

(73) Assignees: Ibiden Co., Ltd., Ogaki-Shi (JP); Athanasios G. Konstandopoulos, Thessaloniki (GR)

( * ) Notice: Subject to any disclaimer, the term of this patent is extended or adjusted under 35 U.S.C. 154(b) by 680 days.

This patent is subject to a terminal disclaimer.

(21) Appl. No.: 11/852,141

(22) Filed: Sep. 7, 2007

(65) Prior Publication Data
US 2008/0087012 A1    Apr. 17, 2008

(30) Foreign Application Priority Data
Oct. 17, 2006    (EP)    .................................. 06386031

(51) Int. Cl.
*F01N 3/00*    (2006.01)
(52) U.S. Cl. .............................. 60/297; 60/276; 60/287; 60/292; 60/295; 60/311; 60/324; 73/114.71; 73/114.75; 73/114.76
(58) Field of Classification Search .................... 60/274, 60/276, 277, 286, 287, 288, 292, 295, 297, 60/311, 324; 73/114.69, 114.71, 114.75
See application file for complete search history.

(56) References Cited

U.S. PATENT DOCUMENTS

| | | | | |
|---|---|---|---|---|
| 5,489,319 A * | 2/1996 | Tokuda et al. .................. | 96/400 |
| 5,651,248 A | 7/1997 | Kawamura | |
| 5,651,250 A | 7/1997 | Kawamura | |
| 5,822,977 A * | 10/1998 | Fukuda et al. ................. | 60/274 |
| 6,779,339 B1 * | 8/2004 | Laroo et al. .................... | 60/297 |
| 7,021,048 B2 * | 4/2006 | Taylor et al. .................. | 60/295 |
| 7,043,914 B2 * | 5/2006 | Ishikawa .................... | 60/605.2 |
| 7,370,474 B2 * | 5/2008 | Minami ........................ | 60/295 |
| 7,484,357 B2 * | 2/2009 | Dollmeyer et al. ............ | 60/274 |
| 7,658,064 B2 * | 2/2010 | Konstandopoulos ......... | 60/297 |
| 2001/0013220 A1 | 8/2001 | Schonauer | |

(Continued)

FOREIGN PATENT DOCUMENTS

EP    0601287    6/1994

(Continued)

OTHER PUBLICATIONS

European Search Report, 06386031.6, mailed May 22, 2007.

*Primary Examiner*—Binh Q. Tran
(74) *Attorney, Agent, or Firm*—Ditthavong Mori & Steiner, P.C.

(57) ABSTRACT

An exhaust gas purifying apparatus includes a primary diesel particulate filter provided in an exhaust line of a diesel engine, a secondary exhaust line branched from the exhaust line from an upstream side of the primary diesel particulate filter, and a secondary diesel particulate filter provided in the secondary exhaust line. The secondary diesel particulate filter has a soot storage capacity smaller than the soot storage capacity of the primary diesel particulate filter. The apparatus further includes a differential pressure measuring part measuring a differential pressure between an inlet and an outlet of the secondary diesel particulate filter. A distance to the secondary diesel particulate filter from a branching point of the secondary exhaust line from the primary exhaust line is about 2 m or less.

14 Claims, 19 Drawing Sheets

U.S. PATENT DOCUMENTS

| | | |
|---|---|---|
| 2008/0087007 A1 | 4/2008 | Konstandopoulos |
| 2008/0087011 A1 | 4/2008 | Konstandopoulos |
| 2008/0087101 A1 | 4/2008 | Konstandopoulos |
| 2008/0098724 A1 | 5/2008 | Konstandopoulos |

FOREIGN PATENT DOCUMENTS

| | | |
|---|---|---|
| JP | 2005-240652 | 9/2005 |
| WO | WO 2004/031548 | 4/2004 |

* cited by examiner

EXHAUST GAS

EXHAUST GAS PURIFYING APPARATUS

CROSS-REFERENCE TO RELATED APPLICATIONS

The present application claims priority under 35 U.S.C. §119 to European Patent Application No. 06386031.6 filed on Oct. 17, 2006. The contents of this European Patent application are incorporated herein by reference in their entirety.

BACKGROUND OF THE MENTION

Field of the Invention

The present invention relates to exhaust gas purifying apparatuses.

FIELD OF THE INVENTION

Conventionally, a diesel particulate filter (DPF) of porous ceramic has been used for collecting particulate matter (PM) primarily of C (carbon) emitted from a diesel engine. With such a diesel particulate filter, there occurs gradual deposition of particulate matter with continual use thereof, and thus, it has been practiced in the art of exhaust gas purifying apparatus that uses a diesel particulate filter to remove the deposited particulate matter by causing a burning process inside the diesel particulate filter periodically and regenerate the diesel particulate filter.

It is preferable that such regeneration of the diesel particulate filter is conducted during the operation of the diesel engine, without replacing or dismounting the filter, and thus, it is practiced in the art to carry out fuel injection in the state that the piston is moving down in the cylinder following combustion to form a high temperature gas (post injection process). Thereby, the deposited particulate matter is burned with the high temperature gas thus formed.

FIG. 1 shows the overall construction of a conventional exhaust gas purifying system of a diesel engine equipped with a diesel particulate filter according to a related art of the present invention.

With the conventional exhaust gas purifying system explained with reference to FIG. 1, it should be noted that such regeneration of filter is conducted each time the vehicle has traveled a predetermined mileage such as 500 km, over the duration of 10 minutes, for example.

In the case the filter regeneration by way of post injection has been conducted impartially, the regeneration is carried out irrespective of actual amount of collection of the particulate matter in the filter. Thus, in order to ensure that there occurs no excessive deposition of the particulate matter in the filter, there is a need to set the interval of filter regeneration to be shorter than what is actually needed for the sake of safety.

On the other hand, there is a known construction of carrying out regeneration of the diesel particulate filter 12B by way of post injection as shown in FIG. 3, in which a differential pressure ΔP is measured between the upstream side and downstream side of the diesel particulate filter 12B and the post injection is carried out when the foregoing differential pressure ΔP has reached a predetermined value. Reference should be made to the U.S. Pat. No. 6,952,920.

Further, U.S. Pat. No. 5,651,248 describes the construction that uses, in addition to the diesel particulate filter, a detection filter and evaluates the amount of the particulate matter collected in the detection filter by measuring the electric resistance. According to this technology, the particulate matter collected by the diesel particulate filter and the particulate matter collected by the detection filter are subjected to burning by using a heater when the detected resistance has decreased below a predetermined value. With this, regeneration of filter is achieved.

The contents of U.S. Pat. Nos. 6,952,920 and 5,651,248 are incorporated herein by reference in their entirety.

SUMMARY OF THE INVENTION

In one aspect, an exhaust gas purifying apparatus of the present invention, including:

a primary diesel particulate filter provided in a primary exhaust line of a diesel engine;

a secondary exhaust line branched from the primary exhaust line from an upstream side of the primary diesel particulate filter;

a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet and an outlet of the secondary diesel particulate filter, wherein a distance to the secondary diesel particulate filter from a branching point of the secondary exhaust line from the primary exhaust line is about 2 m or less.

In another aspect, an exhaust gas purifying apparatus of the present invention, including:

a primary diesel particulate filter provided in a primary exhaust line of a diesel engine;

a secondary exhaust line branched from the primary exhaust line from an upstream side of the primary diesel particulate filter;

a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet and an outlet of the secondary diesel particulate filter, wherein a distance L [m] to the secondary diesel particulate filter from a branching point of the secondary exhaust line from the primary exhaust line is set so as to satisfy the relationship about $50 \leq Q \leq$ about $5000$ ($0 \leq L \leq$ about $1$)

$4950L-4900 \leq Q \leq$ about $5000$ (about $1 \leq L \leq$ about $2$), where Q [ml/min] represents a flow rate of the exhaust gas in the secondary exhaust line represented.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
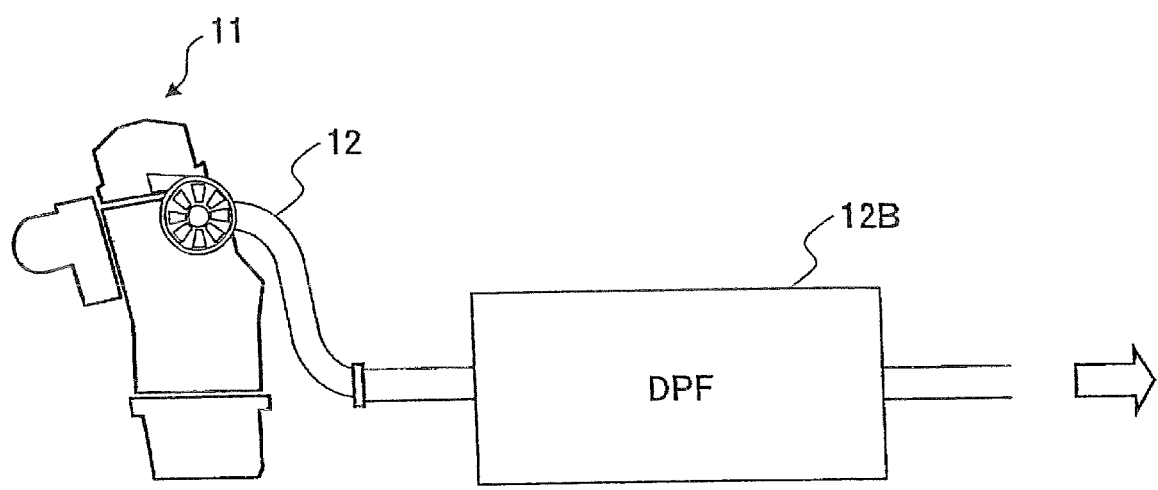
FIG. 1 is a diagram showing an overall engine system that uses a conventional exhaust gas purifying apparatus.

The embodiments will now be described with reference to the accompanying drawings, wherein like reference numerals designate corresponding or identical elements throughout the various drawings.

According to an embodiment, there is provided an exhaust gas purifying apparatus, including: a primary diesel particulate filter provided in a primary exhaust line of a diesel engine; a secondary exhaust line branched from the primary exhaust line from an upstream side of the primary diesel particulate filter; a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet and an outlet of the secondary diesel particulate filter, wherein a distance to the secondary diesel particulate filter from a branching point of the secondary exhaust line from the primary exhaust line is about 2 m or less.

In a preferred embodiment, an exhaust gas is caused to flow through the secondary exhaust line with a flow rate of about 5000 ml/min or less.

In a preferred embodiment, an exhaust gas is caused to flow through the secondary exhaust line with a flow rate of about 5000 ml/min or less and wherein the distance is about 1 m or less.

In a preferred embodiment, the secondary exhaust line includes a flow meter or equivalent meter (e.g. a gas velocity meter).

In a preferred embodiment, the secondary diesel particulate filter includes a temperature measuring part.

In a preferred embodiment, secondary diesel particulate filter includes a heater.

In a preferred embodiment, the exhaust gas purifying apparatus further includes a valve for maintaining a flow rate of an exhaust gas in the secondary exhaust line at a predetermined value.

In a preferred embodiment, the exhaust gas purifying apparatus further includes a holder, and wherein at least one of the differential pressure measuring part, the temperature measuring part, the secondary diesel particulate filter, and the flow meter or equivalent meter (e.g. a gas velocity meter) is accommodated in the holder.

According to an embodiment of the present invention, there is provided an exhaust gas purifying apparatus, including: a primary diesel particulate filter provided in a primary exhaust line of a diesel engine; a secondary exhaust line branched from the primary exhaust line from an upstream side of the primary diesel particulate filter; a secondary diesel particulate filter provided in the secondary exhaust line, the secondary diesel particulate filter having a soot storage capacity smaller than the soot storage capacity of the primary diesel particulate filter; and a differential pressure measuring part measuring a differential pressure between an inlet and an outlet of the secondary diesel particulate filter, wherein a distance L [m] to the secondary diesel particulate filter from a branching point of the secondary exhaust line from the primary exhaust line is set so as to satisfy the relationship about $50 \leqq Q \leqq$ about 5000 ($0 \leqq L \leqq$ about 1)

$4950L - 4900 \leqq Q \leqq$ about 5000 (about $1 \leqq L \leqq$ about 2), where Q [ml/min] represents a flow rate of the exhaust gas in the secondary exhaust line.

In a preferred embodiment, the secondary exhaust line includes a flow meter.

In a preferred embodiment, the secondary diesel particulate filter includes a temperature measuring part.

In a preferred embodiment, the secondary diesel particulate filter includes a heater.

In a preferred embodiment, the exhaust gas purifying apparatus further includes a valve for maintaining a flow rate of an exhaust gas in the secondary exhaust line at a predetermined value.

In a preferred embodiment, the exhaust gas purifying apparatus further includes a holder, and wherein at least one of the differential pressure measuring part, the temperature measuring part, the secondary diesel particulate filter, and the flow meter or equivalent meter (e.g. a gas velocity meter) is accommodated in the holder.

Referring to FIG. 1, a diesel engine 11 has an exhaust line 12, wherein there is provided a diesel particulate filter 12B in the exhaust line 12 for collecting the particulate matter contained in the exhaust gas and emitted from the diesel engine 11.

Figure 2A:
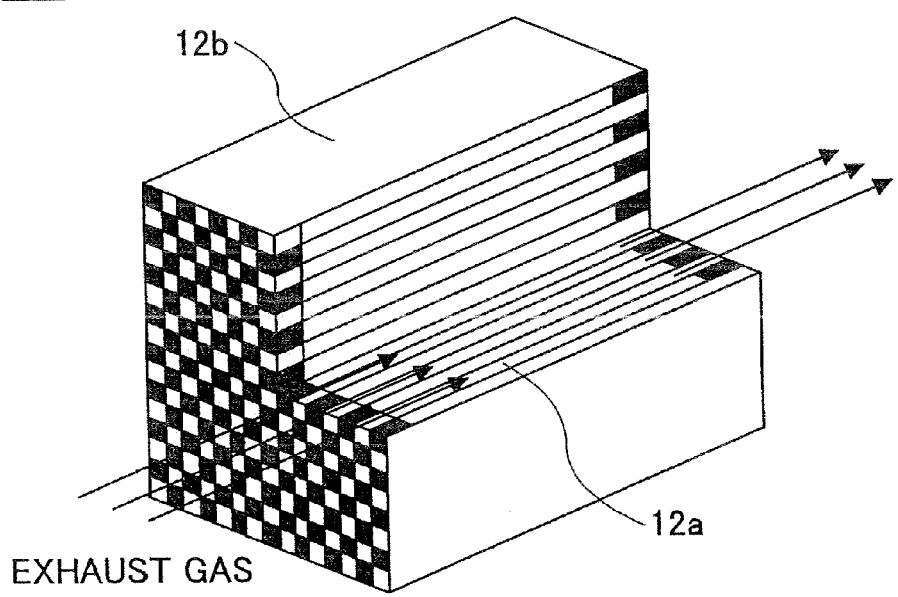
FIG. 2A is a diagram showing a schematic construction of a diesel particulate filter.
Figure 2B:
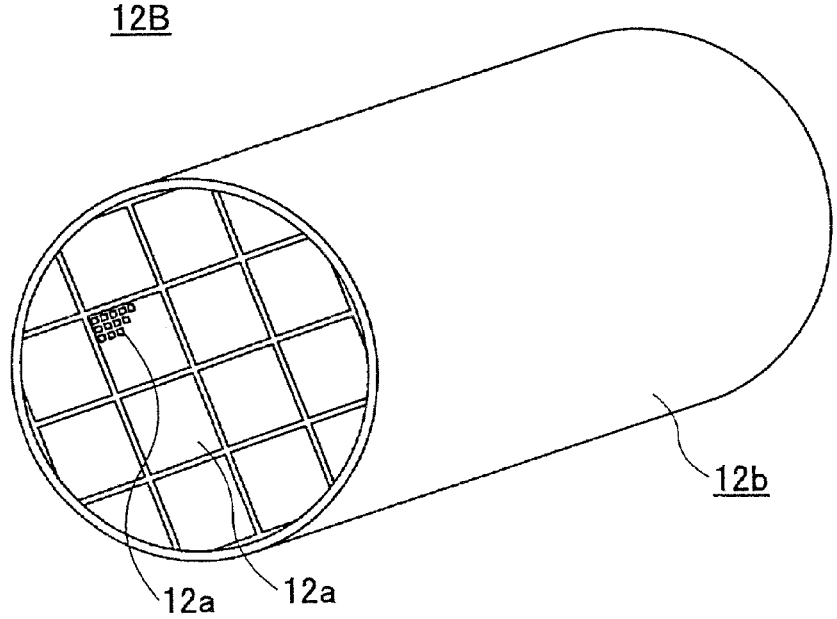
FIG. 2B is a diagram showing a constituting element of the diesel particulate filter.

FIG. 2A shows the outline of the diesel particulate filter 12B while FIG. 2B shows an element that constitutes the diesel particulate filter.

The diesel particulate filter 12B is formed of a filter unit 12A of a porous ceramic, typically of SiC, wherein there are formed a large number of gas passages 12a in the filter unit 12A so as to extend from one end to the other end thereof with a cross-section of 1 mm×1 mm, for example.

Thereby, the diesel particulate filter 12B is formed by binding plural filter units (filter elements) 12A by a seal material (adhesion layer) and machining the peripheral part thereof such that the filter 12B as a whole has a cylindrical form. Further, the peripheral surface of the filter 12B is covered by a seal material (coating layer). There may be a case in which only one unit 12A is used in the diesel particulate filter 12B.

Figure 2C:
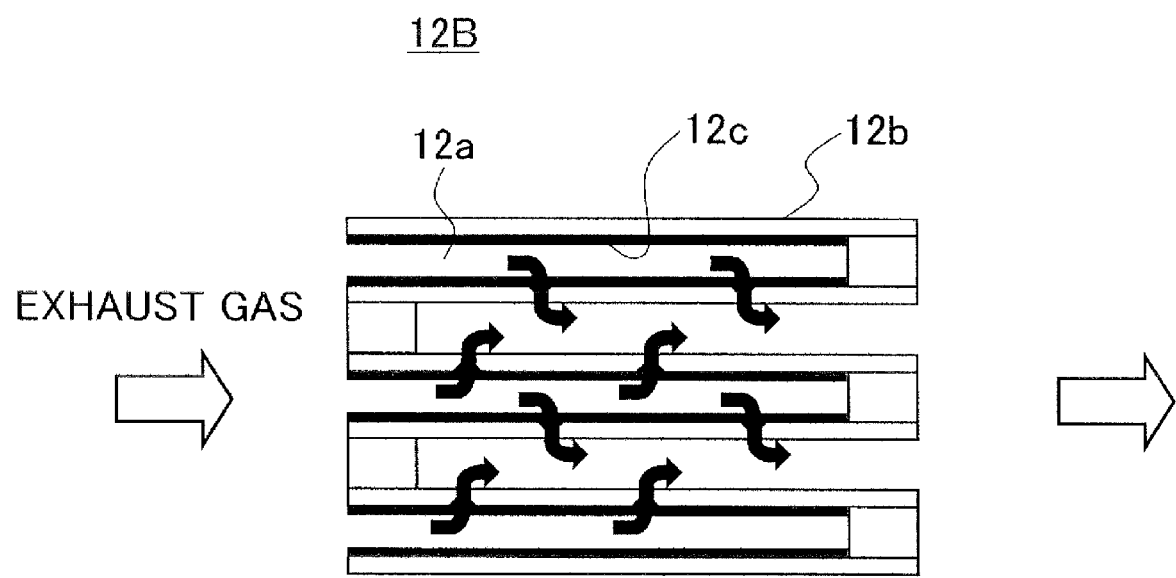
FIG. 2C is a diagram showing the operational principle of the diesel particulate filter.

FIG. 2C shows the principle of the diesel particulate filter 12B.

Figure 2D:
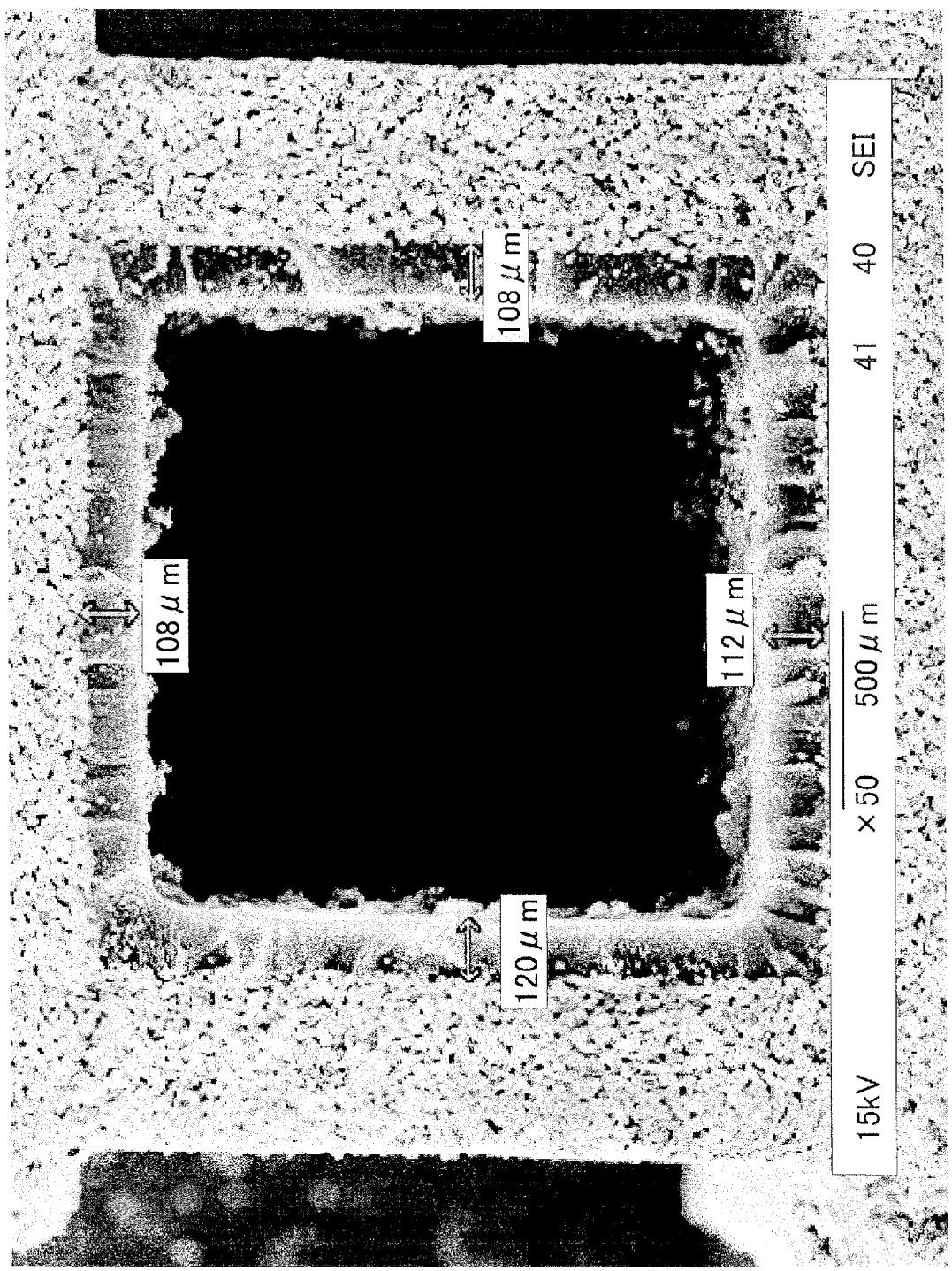
FIG. 2D is a diagram showing the state of the particulate matter collected by the diesel particulate filter.

As shown schematically in FIG. 2C, the plural gas passages 12a have their upstream ends or downstream ends closed alternately with regard to the direction of the exhaust gas flow from the engine, and the exhaust gas introduced to one such gas passage 12a passes to an adjacent gas passage by way of penetration through the porous member 12b of the filter 12B. Thereby, the particulate matter contained in the exhaust gas is collected by the porous member 12b as the exhaust gas penetrates therethrough, and there is caused deposition of the particulate matter 12c on the porous member 12b in the form of layer as shown in FIG. 2D.

Because the diesel particulate filter 12B thus causes deposition of the particulate matter contained in the exhaust gas therein, there is a need of regenerating the filter with suitable timing by conducting a regeneration process (burning of the deposited particulate matter), as described previously.

Figure 3:
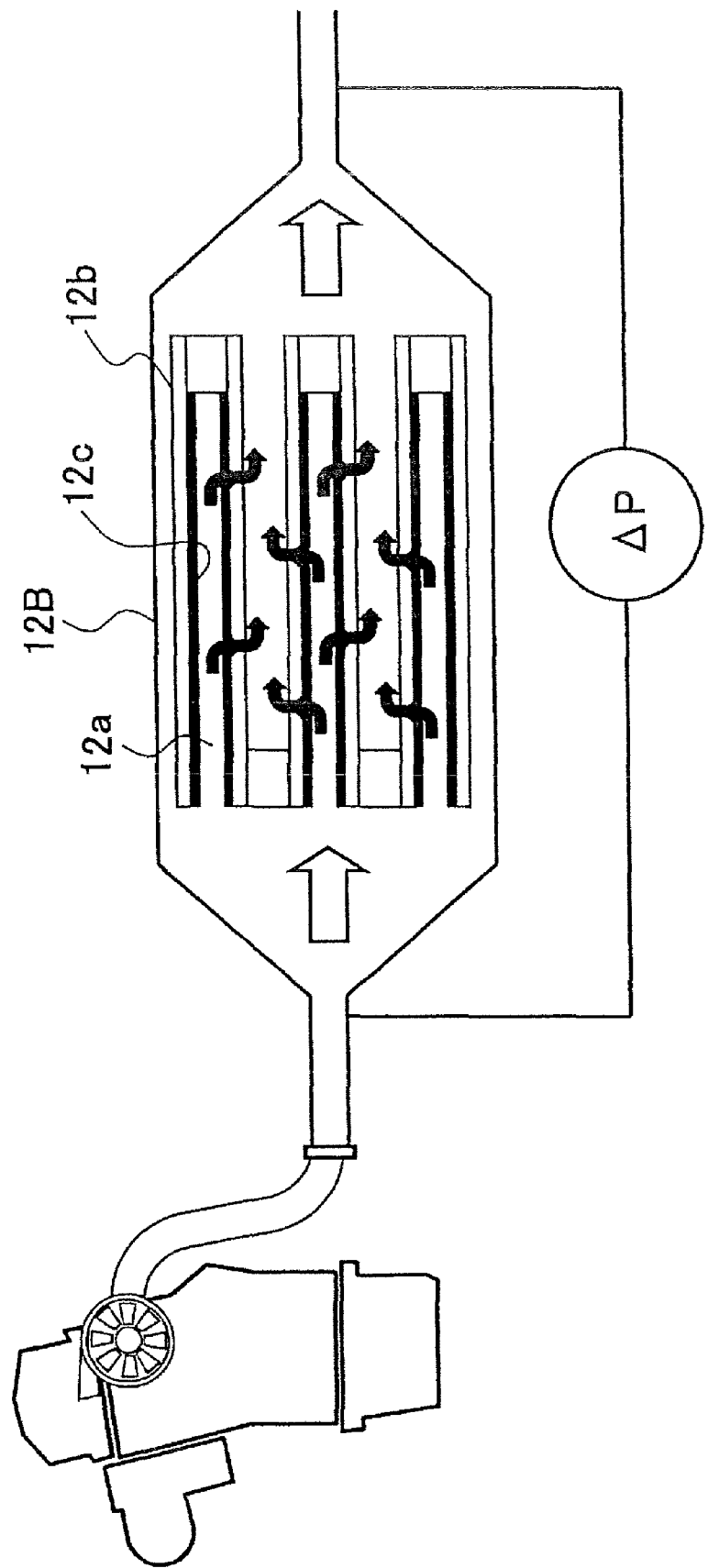
FIG. 3 is a diagram showing the overall construction of an engine system that uses a conventional exhaust gas purifying apparatus according to a related art of the present invention.

According to the conventional construction of FIG. 3, the regeneration of the diesel particulate filter 12B is carried out only when the differential pressure between the upstream side and the downstream side has reached the predetermined value, and unnecessary post injection process is suppressed. Thereby, the fuel efficiency of the vehicle driven with the diesel engine is improved.

Figure 4A:
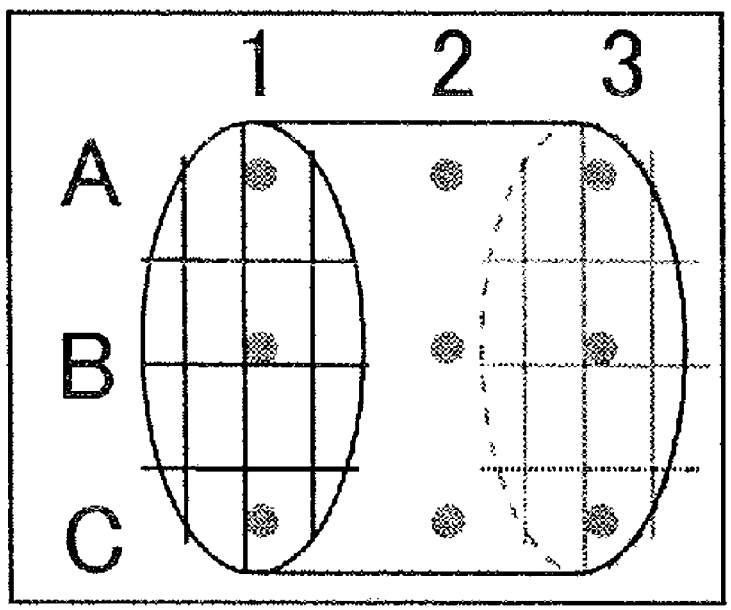
FIG. 4A is a diagram explaining the problem with the exhaust gas purifying apparatus of FIG. 3.
Figure 4A:
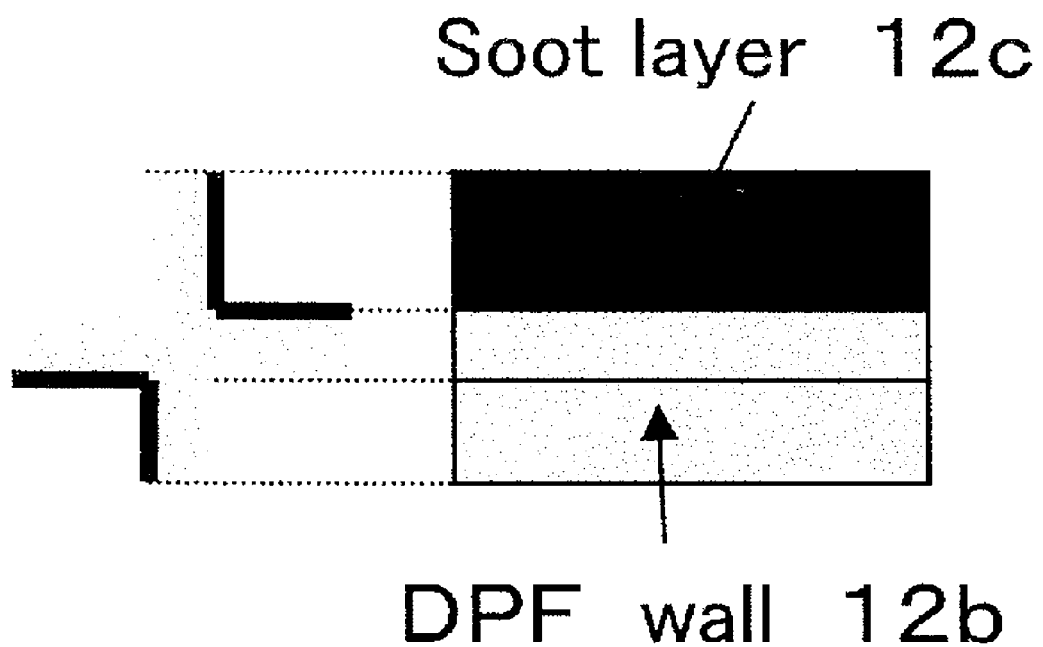
Figure 4B:
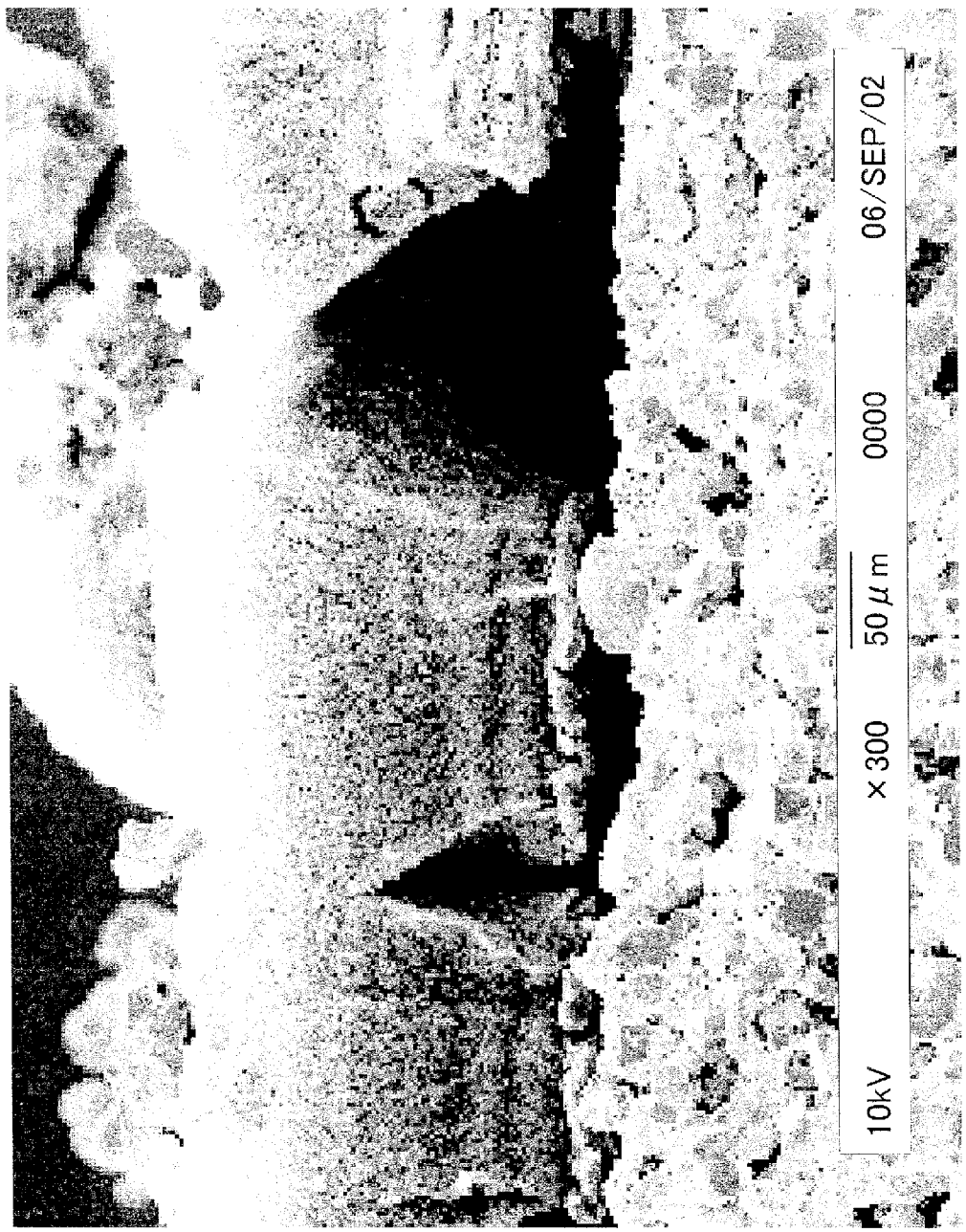
FIG. 4B is a diagram of collected particulate matter at location A1 in FIG. 4A.
Figure 4C:
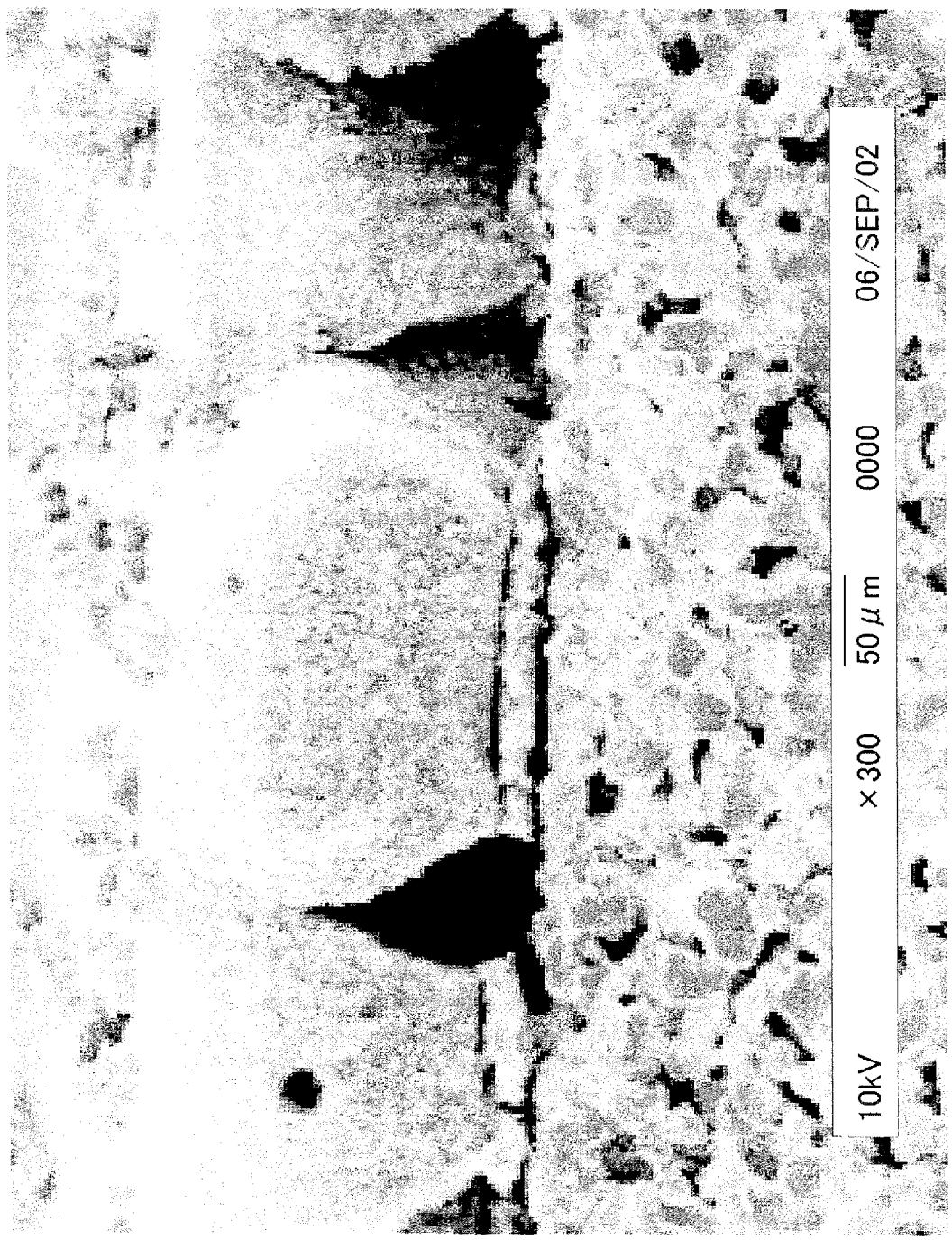
FIG. 4C is a diagram of collected particulate matter at location B2 in FIG. 4A.
Figure 4D:
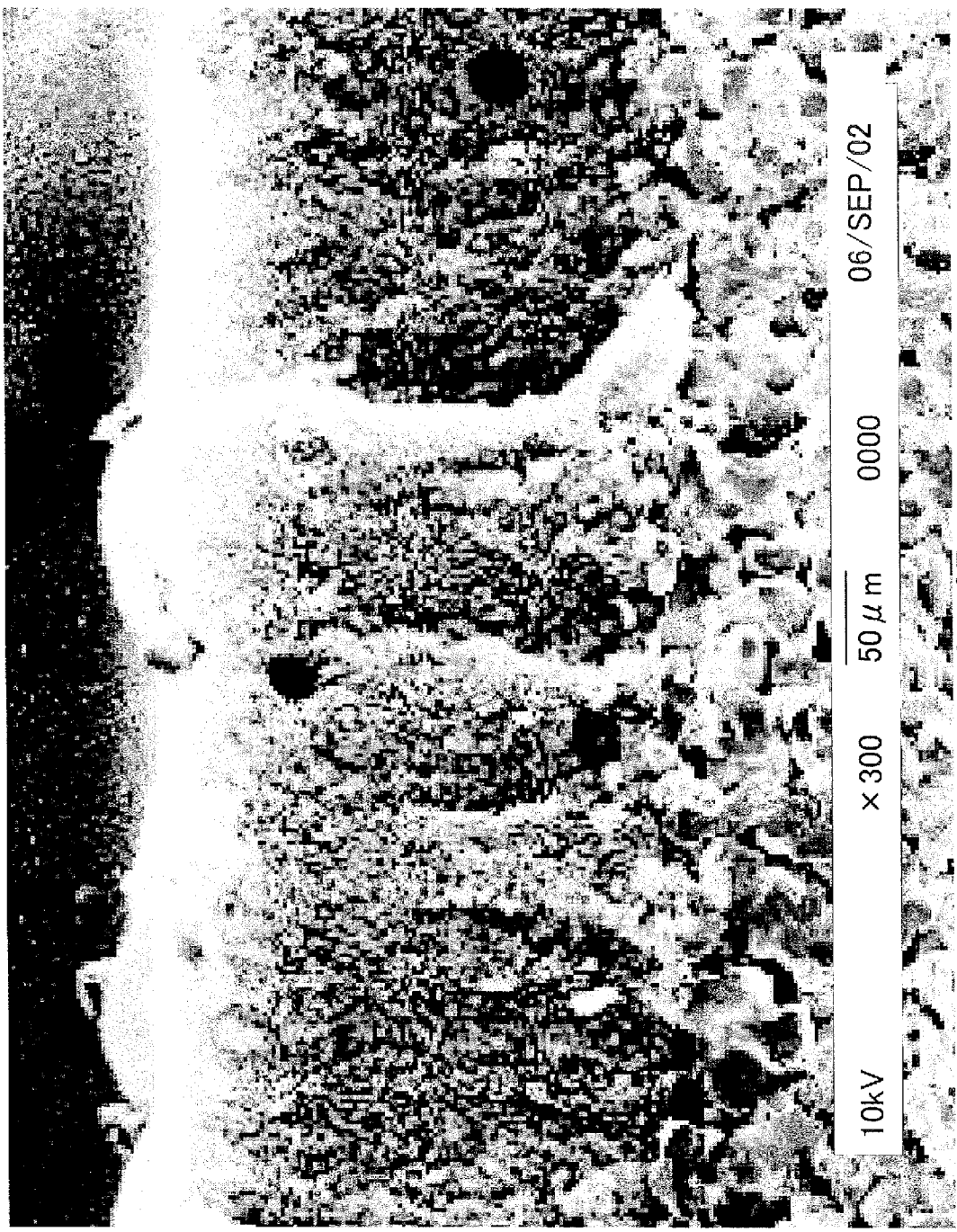
FIG. 4D is a diagram of collected particulate matter at location C3 in FIG. 4A.

Unfortunately, collection of the particulate matter in the diesel particulate filter 12B is not uniform. As shown in FIG. 4A, there is a difference of density or thickness in the collected particulate matter depending on the locations (A,1) (shown in FIG. 4B), (B,1), (C,1), (A,2), (B,2)(shown in FIG. 4C), (C,2), (A,3), (B,3), (C,3) (shown in FIG. 4D) in the filter 12B. Further, it can be seen that there is formed a cavity in the layer of the deposited particulate matter, wherein such a cavity formed in the layer of particulate matter provides as a local passage of exhaust gas. Existence of such a cavity indicates occurrence of uncontrolled burning in the collected particulate matter and indicates further that there has been caused local burning in the collected particulate matter.

Figure 5A:
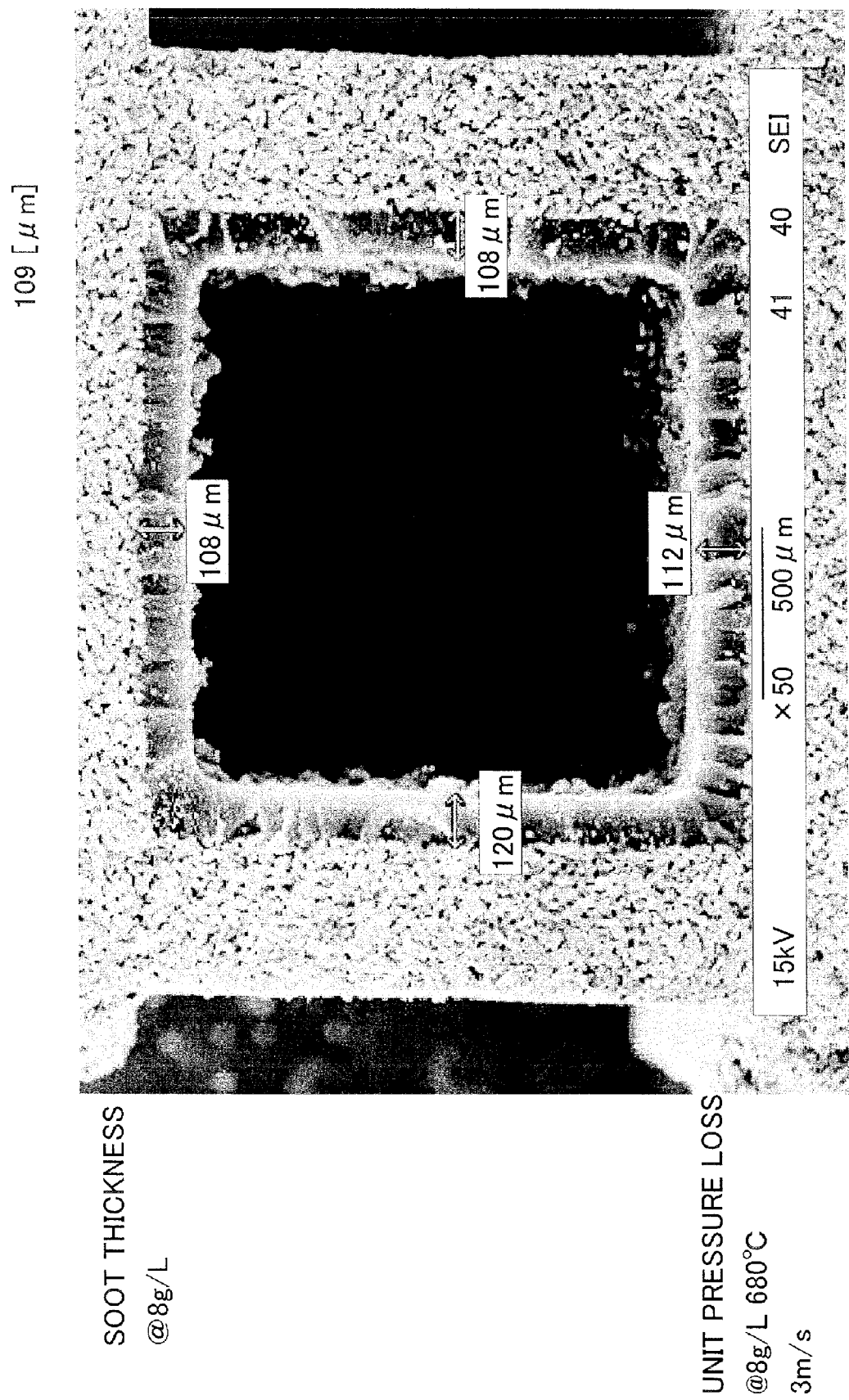
FIGS. 5A, 5B, and 5C are other diagrams explaining the problem of the exhaust gas purifying apparatus of FIG. 3.
Figure 5B:
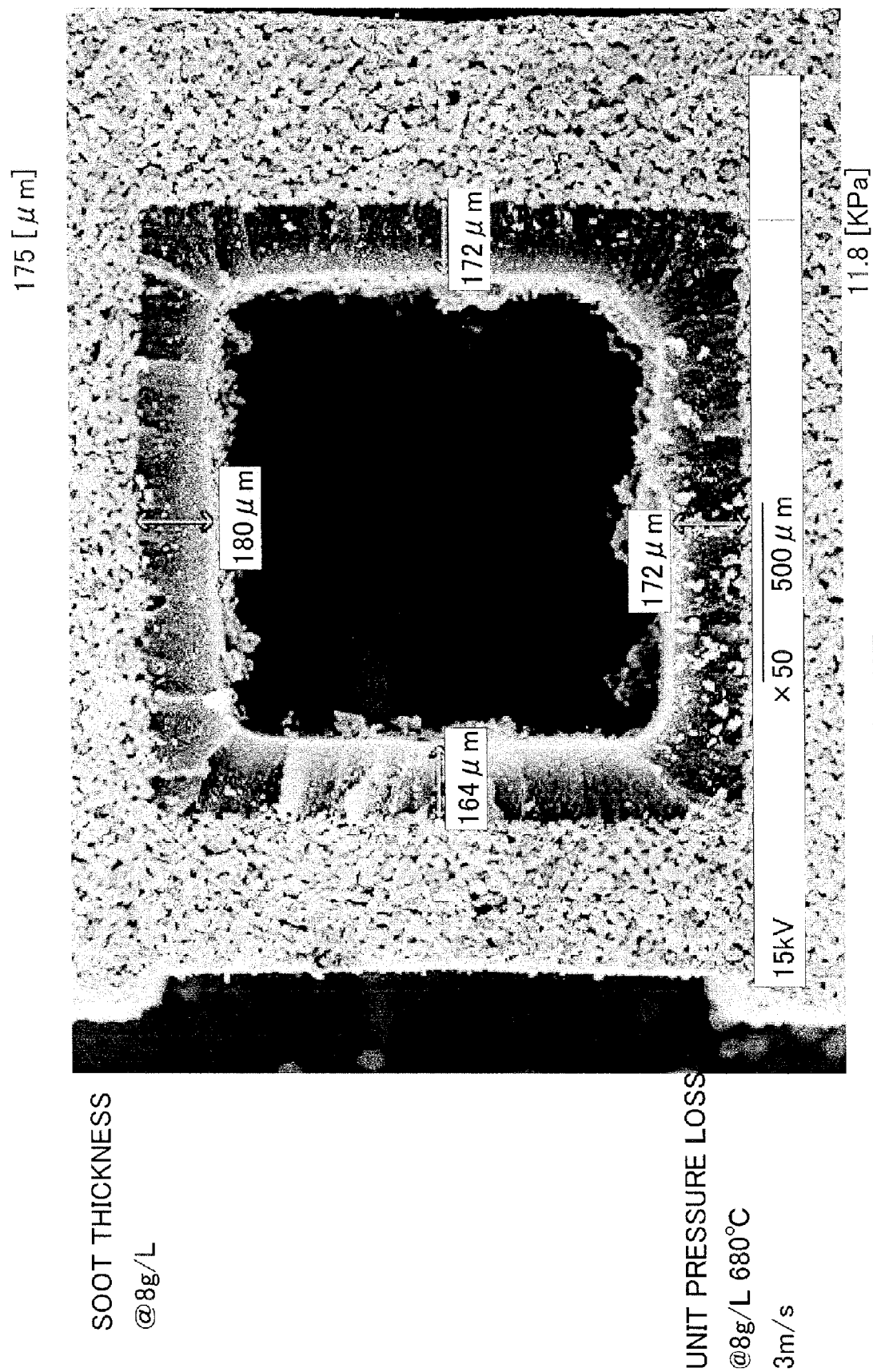
Figure 5C:
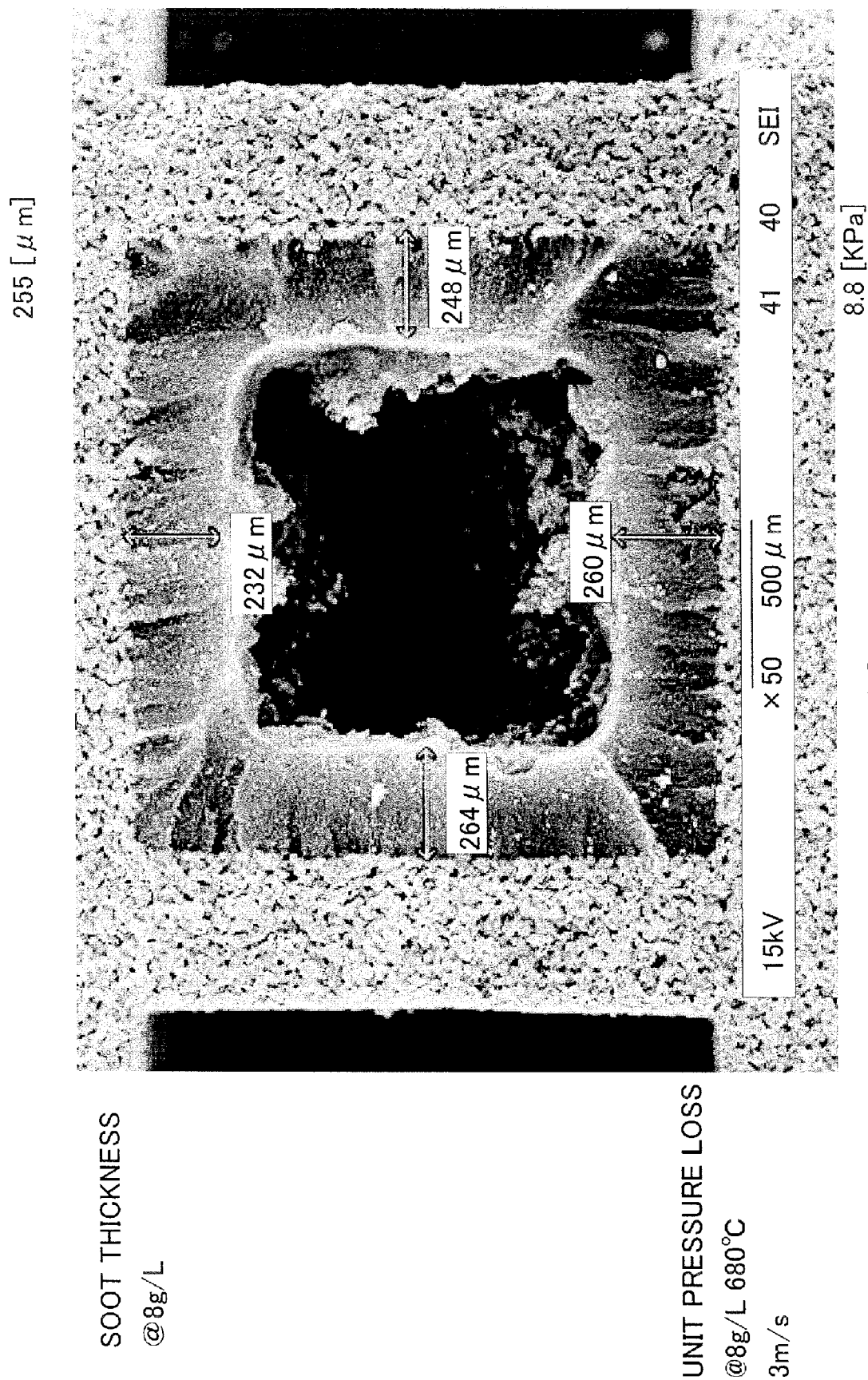

Further, as shown in FIGS. 5A, 5B, and 5C, the density of the collected particulate matter can take different values even when the deposition amount of the particulate matter is identical. FIGS. 5A, 5B, and 5C show that there is caused a large variation in the differential pressure according to the change of the thickness, even when the deposition amount is identical. In the examples of FIGS. 5A, 5B, and 5C, for example, it should be noted that the deposition amount of the particulate matter is 8 g/L throughout. In spite of this, it can be seen in FIGS. 5A, 5B, and 5C that the differential pressure has changed from 15.3 kPa to 8.8 kPa when the thickness of the collected particulate matter has changed from 109 μm to 255 μm. Thus, it can be seen that there is caused about twice as large difference in the differential pressure.

Thus, when such non-uniform deposition or local cavity formation is caused in the particulate matter 12c collected in the conventional construction of FIG. 3, there can be caused an error of as much as ±50% with regard to the evaluation of the actually deposited particulate matter and the differential pressure $\Delta P$, with regard to theoretical calculation values. As a result of such an error, there is caused a large deviation in the relationship between the amount of the actually deposited particulate and the timing of regeneration. Further, in view of the fact that the exhaust gas pressure and the exhaust gas flow rate change with engine load or engine revolution, it has been extremely difficult with the construction of FIG. 3 to detect the deposition amount of the particulate matter in the diesel particulate filter 12B precisely.

This U.S. Pat. No. 5,651,248 has a drawback in that, in addition to the problem that the construction thereof becomes complex because of the need of providing a heater in the diesel particulate filter, there occurs electric power consumption at the time of regeneration of the diesel particulate filter. In order to save the electric power consumption at the time of filter regeneration, the technology of U.S. Pat. No. 5,651,248 selects the timing of executing the filter regeneration such that the regeneration operation is conducted at the time the temperature of the diesel particulate filter is higher than a predetermined temperature, except for the case in which the diesel particulate filter is in the critical state with regard to the deposition of the particulate matter and it is inevitable to carry out regeneration immediately. As a result, there is imposed a restriction on the timing of regenerating operation with this technology, and the degree of freedom of regenerating operation of the particulate detection filter is restricted.

Further, with the technology of the U.S. Pat. No. 5,651,248, it is not possible to use the diesel particulate filter during the regeneration operation carried out by the heater, and because of this, there is provided a reserve diesel particulate filter and switches to this reserve diesel particulate filter during the regeneration process. However, such a construction requires two equivalent diesel particulate filters together with a switching valve, and there arises a problem in that the construction of the exhaust gas purifying apparatus becomes bulky. It is difficult to mount such an exhaust gas purifying apparatus on compact vehicles.

Further, with the technology of the U.S. Pat. No. 5,651,248, regeneration of the detection filter is carried out concurrently with the diesel particulate filter or consecutively to the diesel particulate filter, while such a construction cannot choose the timing of regeneration of the detection filter arbitrarily, and there is a problem that error tends to be caused in the regeneration timing of the diesel particulate filter, depending upon the state of the detection filter.

When regeneration of the diesel particulate filter and regeneration of the detection filter are carried out independently, there is caused a decrease of ventilation resistance in the detection filter upon regeneration thereof, and the exhaust gas starts to flow primarily through the detection filter. Thereby, there is caused an error in the detection of regeneration timing of the diesel particulate filter. From these reasons, the technology of U.S. Pat. No. 5,651,248 carries out regeneration of the detection filter and the regeneration of the diesel particulate filter in synchronization as explained before.

Further, the technology of the U.S. Pat. No. 5,651,248 has a drawback in the points of: (a) ash deposition; and (b) large evaluation error caused by deterioration.

Further, with the technology of the U.S. Pat. No. 5,651,248, there arises another problem from the very principle thereof of measuring electric resistance of electrode for evaluating the deposition amount of the collected particulate matter.

As shown in FIGS. 5A, 5B, and 5C, there can be a situation in which the thickness of the collected particulate matter changes in spite of the fact that the deposition amount thereof is the same. Now, when the thickness of the collected particulate matter is different, it becomes difficult to measure the electrical resistance precisely, and there tends to be caused error in the evaluation of the deposition amount.

Further, in the case there is caused a deposition of ash in the diesel particulate filter or detection filter after burning of the particulate matter, no precise measurement of electrical resistance is possible anymore and there tends to be caused a large error in the evaluation of the deposition amount.

Further, with the use of the detection filter, there is caused degradation in the filter or electrode with time or with use in the ambient of exhaust gas. Particularly, the electrode (terminal formed of a conductive metal) is formed by infiltrating a metal such as Cu, Cr, Ni, or the like, and thus, there is a tendency of causing problems of physical degradation, oxidation degradation and thermal degradation, such as oxidation, adhesion of impurities, cracking, corrosion, and the like.

When there is caused degradation in the filter or electrode, it is no longer possible to carry out precise measurement of the electric resistance and error is tend to be caused in the evaluation of the deposition amount of the particulate matter.

According to the embodiment of the present invention, it becomes possible to measure the deposition amount of particulate matter in the primary diesel particulate filter simply and easily, by using the secondary diesel particulate filter of smaller capacity and hence less prone to cause non-uniform deposition of the particulate matter and by detecting the deposition of the particulate matter in the primary diesel particulate filter by measuring the differential pressure occurring in such a secondary diesel particulate filter. Thereby, it becomes possible to suppress deterioration of fuel efficiency by excessive post injection. Further, with the embodiment of the present invention, it becomes possible to execute the regeneration of the secondary diesel particulate filter independently to the primary diesel particulate filter, and it becomes possible to constantly and precisely measure the deposition amount of the particulate matter in the primary diesel particulate filter by using the secondary diesel particulate filter. Further, it becomes possible to perform precise measurement while eliminating the effect of ash deposition or degradation of the filter or electrode.

Particularly, by providing the secondary diesel particulate filter within the distance of about 2 m from the branching point of the secondary exhaust line from the primary exhaust line, or by disposing the secondary diesel particulate filter such that a distance L [m] to the secondary diesel particulate filter from a branching point of the secondary exhaust line from the primary exhaust line satisfies the relationship about $50 \leq Q \leq$ about 5000 ($0 \leq L \leq$ about 1) and 4950L-$4900 \leq Q \leq$ about 5000 (about $1 \leq L \leq$ about 2) where Q [ml/min] represents a flow rate of the exhaust gas in the secondary exhaust line represented, it becomes possible to achieve precise evaluation of the deposition amount of the particulate matter even in the case the flow rate of the exhaust gas is small.

First Embodiment

Figure 6:
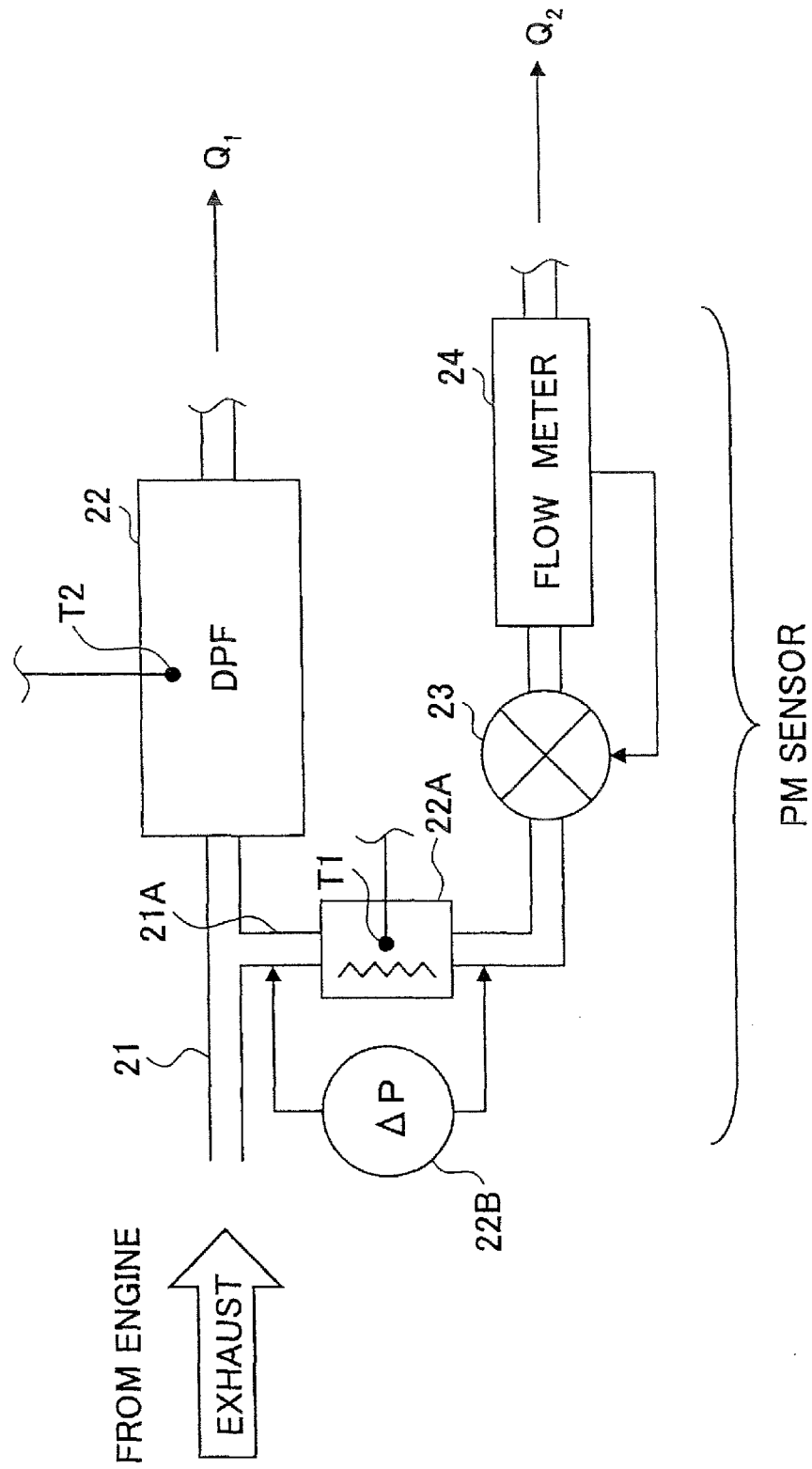
FIG. 6 is a diagram showing the construction of an exhaust gas purifying apparatus according to a first embodiment of the present invention.

FIG. 6 shows the construction of an exhaust gas purifying apparatus 20 according to a first embodiment of the present invention.

Referring to the embodiment of FIG. 6, an exhaust gas from a diesel engine not illustrated is caused to flow into a primary diesel particulate filter (DPF) 22 similar to the one explained previously with reference to FIG. 2A via an exhaust line 21, and the primary diesel particulate filter (DPF) 22 collects the particulate matter in the exhaust gas as explained with reference to FIGS. 2C and 2D.

Further, with the construction of the embodiment of FIG. 6, a secondary exhaust line 21A is branched from the exhaust line 21 from an upstream side of the primary diesel particulate filter (DPF) 22, and a secondary diesel particulate filter 22A is provided to the secondary exhaust line 21A with a volume smaller than the volume of the primary diesel particulate filter (DPF) 22. Further, there is provided a differential pressure gauge 22B for measuring a differential pressure ΔP caused between an inlet and an outlet of the secondary diesel particulate filter 22A. Further, with the construction of FIG. 6, there are provided a flow meter 24 and a control valve 23 in the secondary exhaust line 21A at a downstream side of the secondary diesel particulate filter 22A, wherein the control valve 23 is used for maintaining the flow rate of the exhaust gas in the secondary exhaust line 21A constant based on the measurement made by the flow meter 24. It should be noted that the control valve 23 and the flow mater 24 may be provided anywhere on the secondary exhaust line 21A. Here, it should be noted that the secondary diesel particulate filter 22A, the differential pressure gauge 22B and the flow meter 24 constitutes together a particulate matter (PM) sensor that measures the amount of particulate contained in the exhaust gas. The particulate matter (PM) sensor may be defined to include a temperature measuring part (T1). Further, it is possible to provide a temperature measurement part T2 in the primary diesel particulate filter (DPF) 22.

It should be noted that the temperature measuring part in the exhaust line may be provided in any of: (1) interior of the primary diesel particulate filter, (2) interior of the secondary diesel particulate filter, (3) in a pipe connected thereto, (4) exterior of the primary diesel particulate filter, or (5) exterior of the secondary diesel particulate filter. From the viewpoint of precise measurement of the exhaust gas temperature, the arrangement of (1) or (2) is preferable, wherein the arrangement of (2) is thought more preferable.

In the embodiment of FIG. 6, the primary diesel particulate filter (DPF) 22 is formed of a porous ceramic of SiC, or the like having a porosity of about 35 to about 65% in the form of a honeycomb structure, wherein it can be seen that there are formed gas passages of a rectangular cross-section having a length of 1.1 mm, for example, for each edge in the cross-section taken perpendicular to the gas flow direction, in correspondence to the gas passages 12a of FIG. 2B, wherein the gas passages are arranged with a mutual separation of about 0.3 mm and form together a lattice pattern.

Figure 7A:
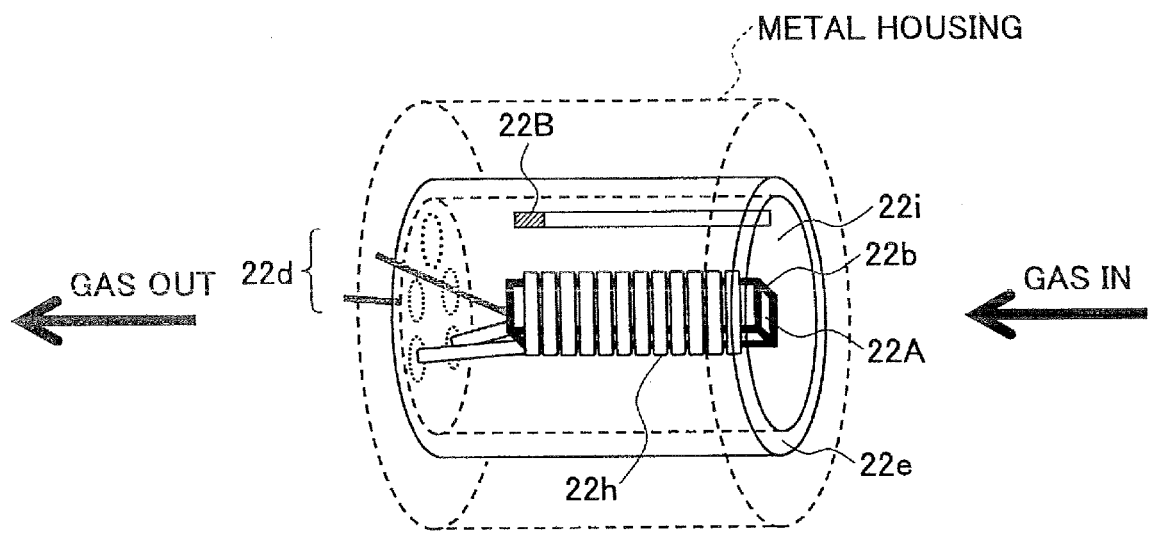
FIG. 7A is a diagram showing the construction of a secondary diesel particulate filter used in FIG. 6.
Figure 7B:
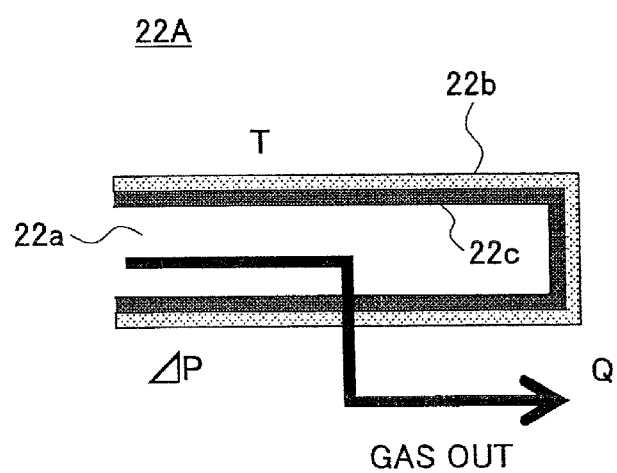
FIG. 7B is a diagram explaining the principle of the secondary diesel particulate filter of FIG. 7A.

FIG. 7A shows the overall construction including the secondary diesel particulate filter 22A, while FIG. 7B shows the principle of the secondary diesel particulate filter 22A.

It should be noted that the secondary diesel particulate filter 22A may be formed of a porous ceramic similar to the primary diesel particulate filter (DPF) 22. In the case the secondary diesel particulate filter is formed of a porous ceramic, it is preferable that the secondary diesel particulate filter includes a secondary diesel particulate filter 22A (cell 22b) of a rectangular form. Therein, there is formed a single gas passage 22a having a volume of about 65 ml or less such as about 0.05 to about 65 ml, or about 5% or less such as about 0.05 to about 5% of the total volume of the exhaust gas passages (corresponding to passage 12a of FIG. 3) in the primary diesel particulate filter (DPF) 22. Alternatively, the gas passage 22a may have a filtration area of about 0.1 to about 1000 cm² (preferably about 1 to about 10 cm²). The gas passage 22a may have a rectangular cross-sectional shape, for example, and is formed in the state that one end thereof is closed (rear end is closed in the case of a cell). Here, it should be noted that the outer shape of the gas passage 22a or the outer shape of the secondary diesel particulate filter 22A (cell 22b) is not necessarily be identical to the cross-sectional shape of the gas passages of the primary diesel particulate filter (DPF) 22, and thus, they can be shaped to any arbitrary shape of circular, square, octahedral, elliptical, or the like. Further, it should be noted that the porous ceramic constituting the secondary diesel particulate filter 22A (cell 22b) is not necessarily be identical with the porous ceramic that forms the primary diesel particular filter (DPF) 22. Further, it should be noted that the secondary diesel particulate filter 22A (cell 22b) may be formed of a material other than ceramics.

By forming the gas passage 22a with the volume of about 5% or less of the exhaust gas passage (corresponds to the passage 12a of FIG. 3) in the primary diesel particulate filter (DPF) 22, or with the volume of 65 ml or less, or with the filtration area of about 0.1 to about 1000 cm² (preferably about 1 to about 10 cm²), it becomes possible to measure the deposition amount of the particulate matter in the primary diesel particulate filter (DPF) 22 with a simple procedure.

The secondary diesel particulate filter 22A (cell 22b) is provided with a temperature measuring part for measuring the exhaust gas temperature T, and a thermocouple 22d is provided for the temperature measuring part. Further, a heater 22h is wound around the secondary diesel particulate filter 22A (cell 22b) for incinerating a soot layer 22c deposited on the inner wall surface and regenerating the secondary diesel particulate filter 22A. Further, the secondary diesel particulate filter 22A (cell 22b), the thermocouple 22d and the heater 22h are accommodated in a cylindrical holder 22e of $SiO_2$—$Al_2O_3$, or the like, by interposing an insulator 22i of $Al_2O_3$, or the like, and there is provided a diaphragm pressure gauge 22B in the holder 22e for measuring the differential pressure ΔP, in such a manner that the exhaust gas in the secondary exhaust line 21A is supplied to the pressure gauge 22B. The holder 22e is accommodated in a metal housing and is provided to the secondary exhaust line as the particulate matter (PM) sensor. The holder 22e may also be provided inside the pipe of the secondary exhaust line or may be provided inside the secondary exhaust line in the state accommodated in the metal housing.

Thus, when the exhaust gas in the secondary exhaust line 21A is introduced to the exhaust passage 22a of the secondary diesel particulate filter 22A (cell 22b), the exhaust is caused to flow outside the cell through the wall surface of the secondary diesel particulate filter 22A (cell 22b), and the particulate matter in the exhaust gas is collected similarly to the case of FIG. 2C. Thereby, the particulate matter deposits on the inner surface of the secondary diesel particulate filter 22A (cell 22b) to form a layer 22c.

With the present embodiment, the deposition amount of the particulate 22c thus collected and deposited on the inner wall surface of the diesel particulate filter 22 is calculated from the pressure difference ΔP and the temperature T and flow rate Q of the exhaust gas thus obtained by using the equation (1) below.

Figure 8:
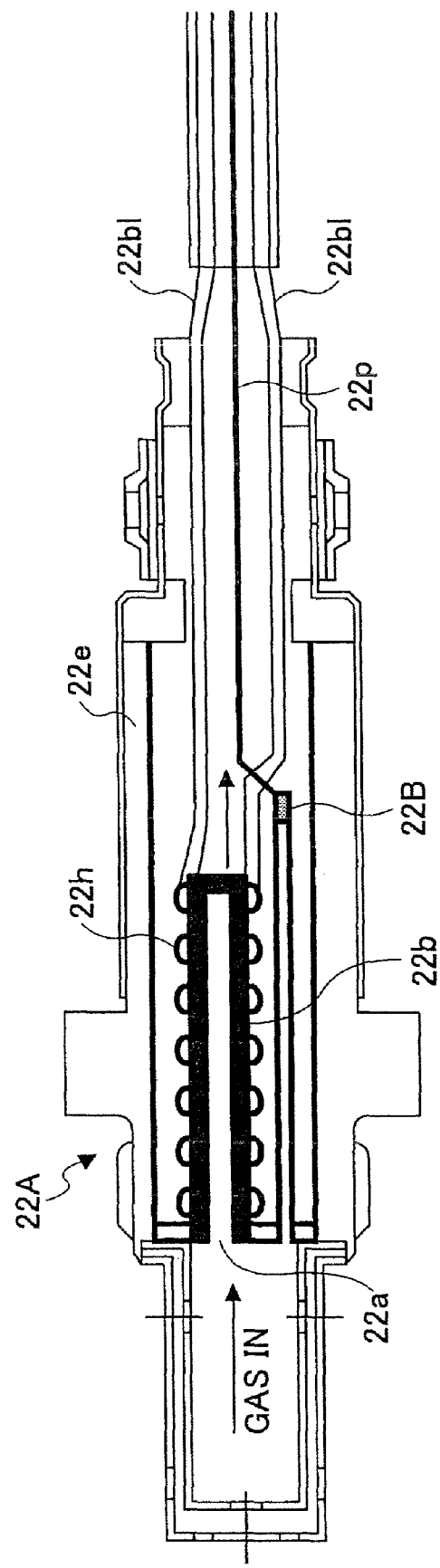
FIG. 8 is a diagram showing the construction of a particulate matter (PM) sensor that uses the secondary diesel particulate filter of FIG. 6.

FIG. 8 shows a more detailed construction of the secondary diesel particulate filter 22A of FIG. 6.

Referring to FIG. 8, the exhaust gas in the secondary exhaust line 21A is supplied to the gas passage 22a in the secondary diesel particulate filter 22A (cell 22b) as represented by an arrow and is discharged, after passing through the cell, in the lateral direction or rear direction. Thereby, the heater 22h on the secondary diesel particulate filter 22A (cell 22b) is driven by the electric power supplied by a drive line 22b1 and causes incineration in the particulate matter 22c collected by the secondary diesel particulate filter 22A (cell 22b). Further, the output signal of the diaphragm pressure gauge 22B is supplied to a control circuit via a signal line 22p.

With the secondary diesel particulate filter 22A of FIGS. 7A and 7B, the amount of soot load of the particulate matter collected in the secondary diesel particulate filter is calculated according to an equation of the form $$\Delta P = \text{function(Flow, Temperature, Soot load, Geometry)}$$

with a preferred example shown below (although other expressions can be also employed) according to which the thickness W[m] of a layer 22c of the particulate matter collected in the secondary diesel particulate filter is calculated according to $$\Delta P = \frac{\mu Q}{2 V_{trap}}(\alpha + W_s)^2 \quad (1)$$

$$\left[\frac{W_s}{K_w \alpha} + \frac{1}{2 K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right)\right] +$$

$$\frac{\rho Q^2 (\alpha + Ws)^4}{V_{trap}^2}\left[\frac{\beta Ws}{4} + 2\zeta\left[\frac{L}{\alpha}\right]^2\right]$$

wherein ΔP represents the differential pressure [Pa], μ represents a kinetic viscosity coefficient, Q represents the flow rate of the exhaust gas represented in terms of [m³/h], α represents an edge length of the cell, ρ represents a specific gravity of the exhaust gas, $V_{trap}$ represents a filter volume, Ws represents a wall thickness, Kw represents a well permeability, $K_{soot}$ represents a permeability of the collected particulate matter layer, W represents the thickness of the collected particulate matter layer, F is a numerical coefficient (=28.454), L represents an effective filter length, β represents the Forchheimer coefficient of the porous wall, q represents the inertial loss coefficient of the exhaust gas entering and exiting the secondary diesel particulate filter.

Next, the mass $m_{soot}$ of the particulate matter collected by the cell 21b is obtained according to $$W = \frac{\alpha - \sqrt{\alpha^2 - \frac{m_{soot}}{N_{cells} \times L \times \rho_{soot}}}}{2} \quad (2)$$

wherein $m_{soot}$ represents the mass [g] of the particulate matter collected, while $N_{cells}$ represents an aperture number of the cell at the inlet side, and $\rho_{soot}$ represents the density of the collected particulate matter.

Thus, a collection amount per unit time, PM [g/h] is obtained by dividing $m_{soot}$ by the time [h] as measured from the previous regeneration of the secondary diesel particulate filter 22A.

Once the mass PM [g/h] of the particulate matter deposited in a unit time is obtained, the concentration of the particulate matter in the exhaust gas, $PM_{conc}$ [g/m³], is obtained by using the flow rate Q2 [m³/h] of the exhaust gas passing through the secondary diesel particulate filter 22A as $$PM [g/h] = PM_{conc} [g/m^3] \times Q2 [m^3/h]. \quad (3)$$

Because the concentration $PM_{conc}$ of the particulate matter in the exhaust gas takes the same value in the secondary exhaust line 21A and also in the exhaust lien 21, the amount of the particulate matter $PM_{enter\,full\,filter}$ [g/h] that has flowed into the diesel particulate filter 22 is obtained from the mass PM [g/h] of the particulate matter deposited per unit time, as $$PM_{enter\,full\,filter} [g/h] = PM_{conc} [g/m^3] \times Q1 [m^3/h] \quad (4)$$

Further, from this, the amount of the particulate matter deposited in the filter is obtained by taking into consideration the collection efficiency of the filter. In the foregoing, Q1 represents the flow rate of the exhaust gas passing through the primary diesel particulate filter (DPF) 22. Q1 may be obtained by actual measurement or estimated from the operational state of the engine.

Figure 9:
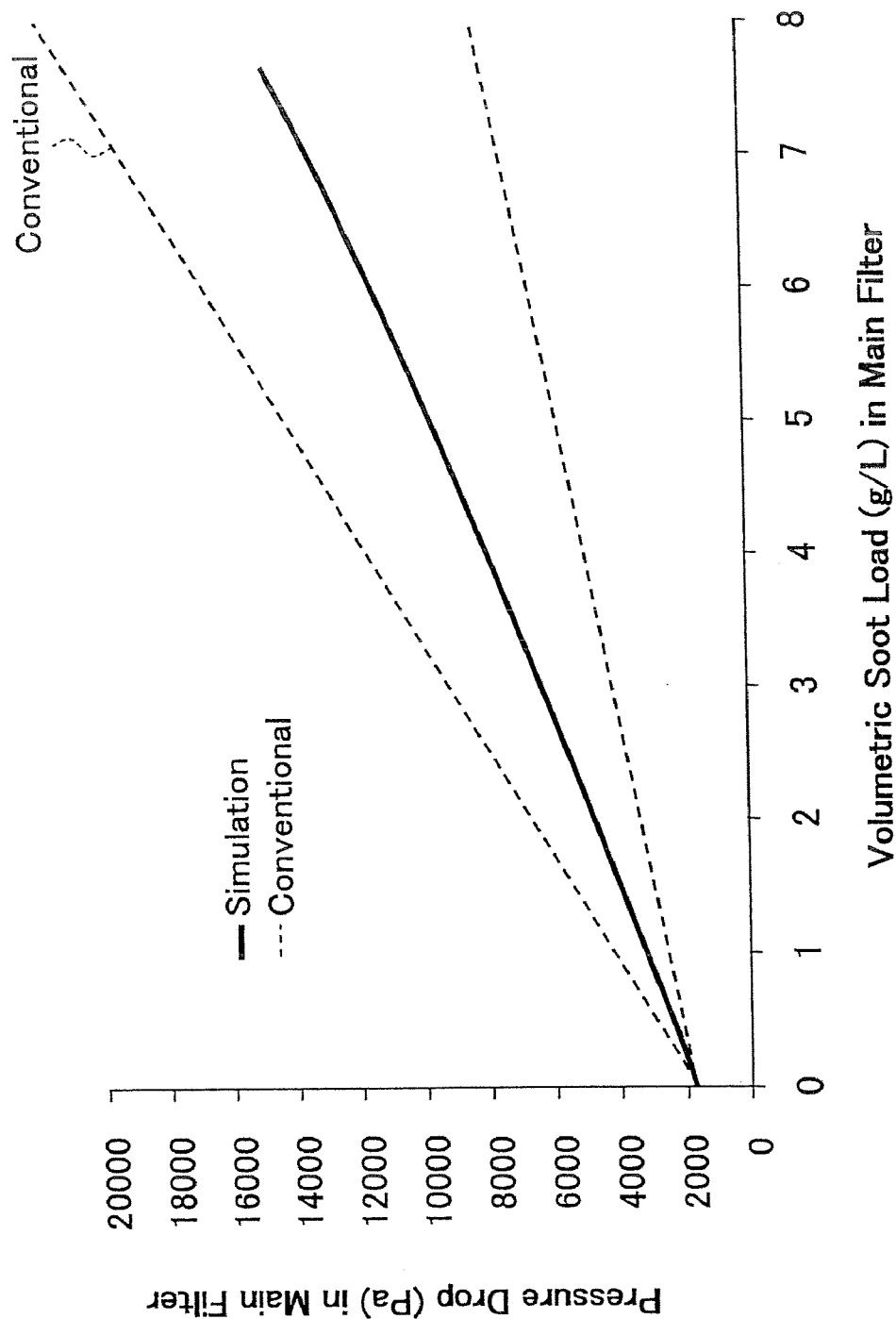
FIG. 9 is a diagram explaining the effect of the embodiment the invention.

FIG. 9 shows the relationship between the differential pressure occurring across the primary diesel particulate filter (DPF) 22 of the exhaust gas purifying apparatus of the embodiment FIG. 6 and the deposition amount of the particulate matter in the primary diesel particulate filter (DPF) 22, wherein it should be noted that the continuous line shows the case in which the deposition amount of the particulate matter in the main diesel particulate filter 22 is obtained by using the secondary diesel particulate filter 22A and Equations (1) to (4). On the other hand, the dotted line represents the case in which the deposition amount of the particulate matter in the primary diesel particulate filter (DPF) 22 is obtained directly from the differential pressure across the primary diesel particulate filter (DPF) 22.

Referring to FIG. 9, it can be seen that there can occur a variation, and hence error, of as much as about ±50% in the differential pressure across the primary diesel particulate filter (DPF) 22 when compared at the same deposition amount of the particulate matter.

Contrary to this, it is possible to obtain the amount of deposition of the particulate matter collected by the primary diesel particulate filter (DPF) 22 within the error of about +10% by obtaining the differential pressure $\Delta P$ across the secondary diesel particulate matter and by using Equations (1) to (4).

Thus, according to the embodiment of the present invention, it becomes possible to evaluate the deposition amount of the particulate matter in the primary diesel particulate filter (DPF) 22 in the exhaust gas purifying apparatus of FIG. 6 precisely by measuring the differential pressure $\Delta P$ formed in the secondary diesel particulate filter 22A of small volume, and it becomes possible to execute the regeneration of the primary diesel particulate filter (DPF) 22 with optimum timing by way of carrying out the post injection based on the foregoing result. With this, unnecessary post injection is avoided and the fuel efficiency of the vehicle is improved.

In the construction of FIG. 6, it is possible to use a known Vencheri flow meter or hotwire flow meter, wherein the flow meter 24 can control the exhaust gas flow rate in the secondary exhaust line 21A generally constant within the range of about 50 to about 6000 ml/min, for example. With this, one-sided flow of the exhaust gas through the secondary exhaust line 21A is avoided, and it becomes possible to obtain the deposition amount of the particulate matter in the primary diesel particulate filter (DPF) 22 from the deposition amount obtained by using the secondary diesel particulate filter 22A, with further improved precision.

Here, it should be noted that the "differential pressure measuring part measuring a differential pressure between an inlet and an outlet of said secondary diesel particulate filter" includes not only the differential pressure gauge that measures the differential pressure between the inlet side and the outlet side of the secondary diesel particulate filter 22A but also the construction that uses a pressure gauge only at the outlet side of the diesel particulate filter 22A. With such a construction, the pressure value of the initial state (the state immediately after regeneration) is memorized and the differential pressure is calculated by measuring the pressure for the state in which there occurred deposition of the particulate material in the secondary diesel particulate filter 22A and by subtracting the pressure value thus obtained from the memorized initial pressure value.

Further, it is also possible to provide a flow meter or a flow velocity meter at the inlet side and the outlet side or only at the outlet side of the secondary diesel particulate filter for measuring the differential pressure. With such a construction, the differential pressure is obtained from the reading value of the flow meters or flow velocity meters provided at the inlet side and the outlet side of the secondary diesel particulate filter. Alternatively, the differential pressure may be obtained from the reading value of the flow meter, the flow velocity meter or the like at the outlet side of the secondary diesel particulate filter, by comparing the reading value for the initial state (the state immediately after regeneration) and the reading value for the state where there is caused deposition of the particulate matter in the secondary diesel particulate filter.

The embodiment of the present invention has the feature of obtaining the amount of the particulate matter deposited in the primary diesel particulate filter (DPF) 22 from the differential pressure obtained for the secondary diesel particulate filter 22A by using Equation (1), and thus, any instruments including those that are used conventionally for measuring a differential pressure may be used for measuring the differential pressure of the secondary diesel particulate filter.

Second Embodiment

Figure 10:
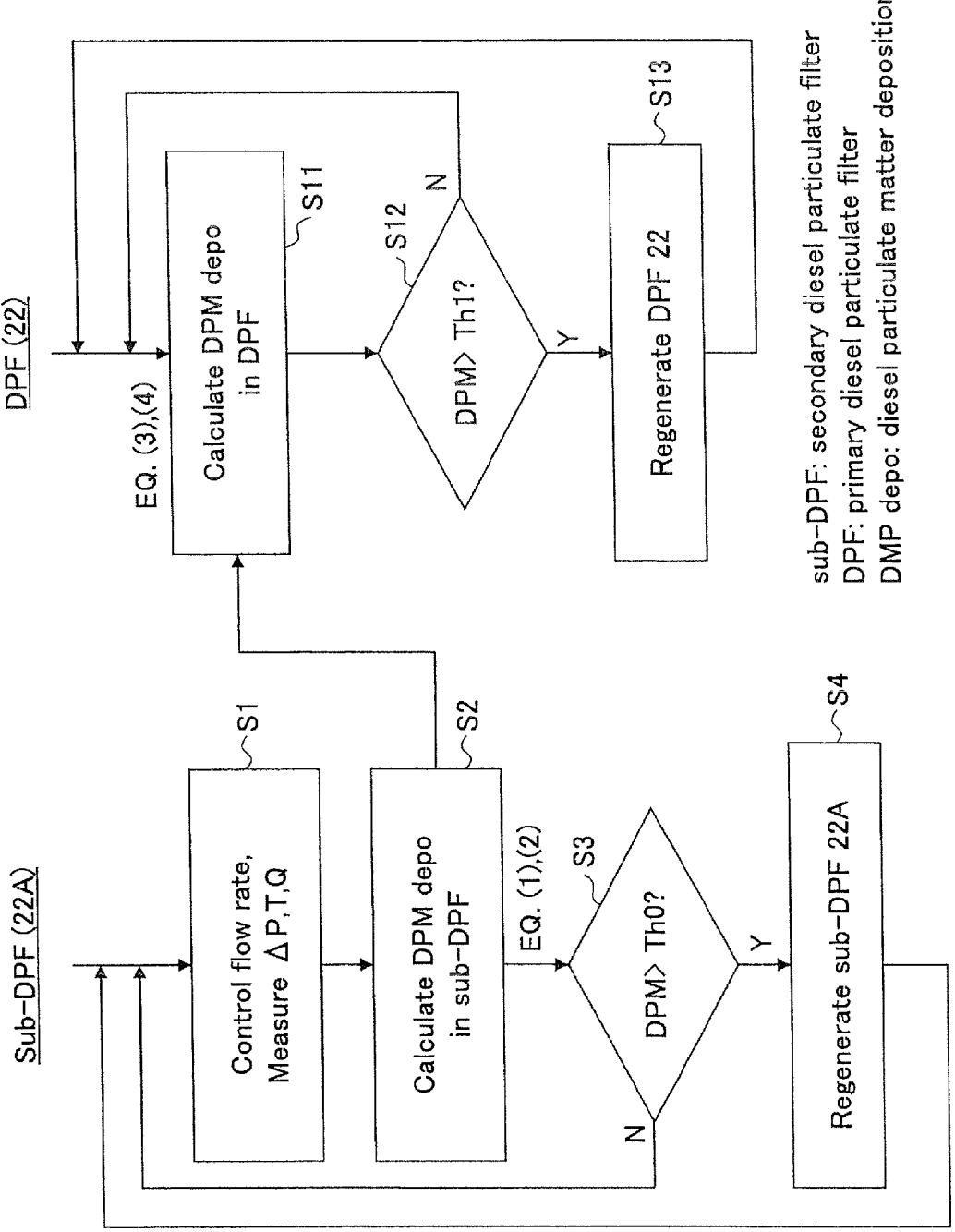
FIG. 10 is a flow chart explaining the regeneration operation of the diesel particulate filter in the exhaust gas purifying apparatus according to a second embodiment of the present invention.

FIG. 10 is a flowchart showing the exhaust gas purifying method according to a second embodiment of the present invention that uses the exhaust gas purifying apparatus of the embodiment of FIG. 6.

Referring to FIG. 10, the flow rate in the secondary exhaust line 21A is set to a predetermined value in the range of about 50 to about 6000 ml/min in the step 1 by using the flow meter 24, or in some cases by using the valve 23, and the differential pressure $\Delta P$ across the secondary diesel particulate filter 22A is detected by the differential pressure gauge 22B. Further, the temperature of the exhaust gas is detected by using the temperature measuring part T1.

Next, in the step 2, the layer thickness W of the particulate matter collected by the secondary diesel particulate filter 22A is obtained from the differential pressure $\Delta P$ detected in the step 1 according to Equation (1). Here, it should be noted that the temperature T of the exhaust gas may be obtained by using the temperature measuring part T2 of the primary diesel particulate filter (DPF) 22 in place of using the temperature measuring part T1 of the secondary diesel particulate filter 22A. Further, the temperature T may be calculated from the temperatures of the temperature measuring parts T1 and T2 (in the form of average value, maximum value, minimum value, for example). From the viewpoint of calculating the amount of the particulate matter more precisely, it is preferable to use the temperature measuring part T1 of the secondary diesel particulate filter 22A. For the thermometer, a thermocouple may be used, while it is also possible to use anything as long as it can measure the temperature. While it is preferable to measure the temperature of the exhaust gas inside the exhaust pipe, it is also possible to measure the temperature of the filter or the cell.

Further, in the step 2, the mass $m_{soot}$ of the particulate matter collected by the cell 21b is obtained from the layer thickness W detected in the step 1 by using Equation (2) mentioned previously.

Further, in the step 3, it is judged whether or not the mass $m_{soot}$ of the layered particulate matter deposited in the secondary diesel particulate filter 22A (cell 22b) of the secondary diesel particulate filter 22A has exceeded a predetermined threshold Th0, and if the result is NO, the process returns to the step 1.

When the mass $m_{soot}$ of the layered particulate matter deposited in the secondary diesel particulate filter 22A (cell 22b) of the secondary diesel particulate filter 22A has exceeded the predetermined threshold Th0 in the step 3, the heater 22h is activated in the step 4 and the particulate matter 22c is removed by burning.

Meanwhile, in the process of FIG. 10, the concentration PM of the particulate matter in the exhaust gas is obtained in the step 11 from Equation (3) while using the mass $m_{soot}$ of the collected particulate matter in the secondary diesel particulate filter 22A (cell 22b) obtained in the step 2, and the deposited amount $PM_{enter\,full\,filter}$ of the particulate deposited in the principal diesel particulate filter 22 is obtained from Equation (4) and from the collection efficiency of the primary diesel particulate filter (DPF) 22.

Thus, in the step 12, it is judged whether or not the deposited amount $PM_{enter\,full\,filter}$ of the particulate matter in the primary diesel particulate filter (DPF) 22 exceeds a predetermined threshold value Th1, and if the result of judgment is NO, the operation returns to the step S11.

In the event it is judged in the step 12 that the deposited amount $PM_{enter\,full\,filter}$ of the particulate matter in the primary diesel particulate filter (DPF) 22 exceeds the predetermined threshold value Th1, post injection is executed in the step 13 by controlling an engine control unit (ECU), and the deposited particulate matter in the primary diesel particulate filter (DPF) 22 is removed by burning. Thereby, regeneration of filter is achieved.

With the process of FIG. 10, it is possible to carry out the regeneration of the secondary diesel particulate filter 22A and the primary diesel particulate filter (DPF) 22 independently, and thus, it is possible to always maintain the deposited amount of the particulate matter 22c, or the amount of the soot layer, in the secondary diesel particulate filter 22A (cell 22b), which constitutes the secondary diesel particulate filter 22A, to be a small value of about 0.5 g/l or less. With such a construction, it becomes possible to improve the sensitivity of the particulate matter sensor that uses the secondary diesel particulate filter 22A.

With the construction of the embodiment of FIG. 6, in which the valve 23 is provided to the secondary exhaust line 21A, there is caused no such a situation that the exhaust gas flows predominantly through the secondary diesel particulate filter where regeneration has been made even when the regeneration of the secondary diesel particulate filter 22A is conducted independently to the primary diesel particulate filter (DPF) 22, and there is caused no error in the evaluation of the deposited amount of the particulate matter in the primary diesel particulate filter (DPF) 22.

Thereby, it should be noted that there is no need for the valve 23 to maintain the exhaust gas flow rate in the secondary exhaust line 21A exactly at a constant level but it is just sufficient to avoid extreme deviation of the exhaust gas flow to the secondary exhaust line 21A.

Thus, in the second embodiment noted above, the differential pressure ΔP, the exhaust gas temperature T and the exhaust gas flow rate Q are measured (step 1), the mass of the particulate matter collected by the secondary diesel particulate filter is obtained by using Equations (1) and (2) from the foregoing result of measurement (step 2), and the amount of the particulate matter collected by the primary diesel particulate filter is obtained from the amount of the particulate matter collected in the secondary diesel particulate filter by using Equations (3) and (4) and further using the collection efficiency of the primary diesel particulate filter (step 11).

In FIG. 10, and also in FIG. 11 to be explained below, the primary diesel particulate filter (DPF) 22 is designated as DPF while the secondary diesel particulate filter 22A is designated as sub-DPF. Further, the deposition of diesel particulate matter is designated as DPM depo.

Figure 11:
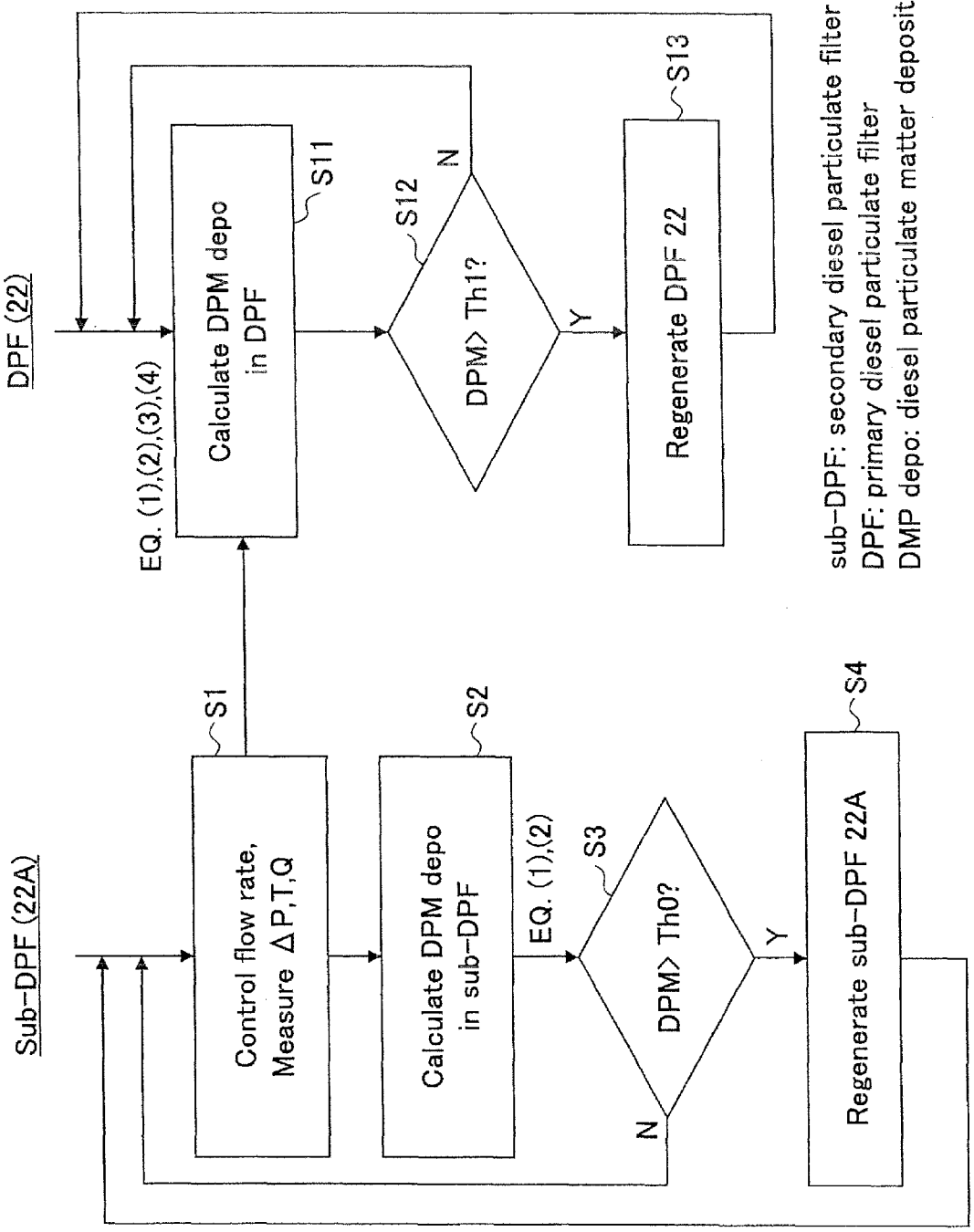
FIG. 11 is a flowchart explaining another regeneration operation of the diesel particulate filter of the exhaust gas purifying apparatus according to the second embodiment of the present invention.

On the other hand, the process of obtaining the amount of the particulate matter collected in the primary diesel particulate filter may be modified as shown in FIG. 11.

Thus, in FIG. 11, the process for obtaining the amount of the particulate matter collected by the primary diesel particulate filter (step 11) is carried out in parallel with the process of obtaining the amount of the particulate matter collected by the secondary diesel particulate filter (step 2), while using the result of measurement obtained in the step 1.

Figure 12:
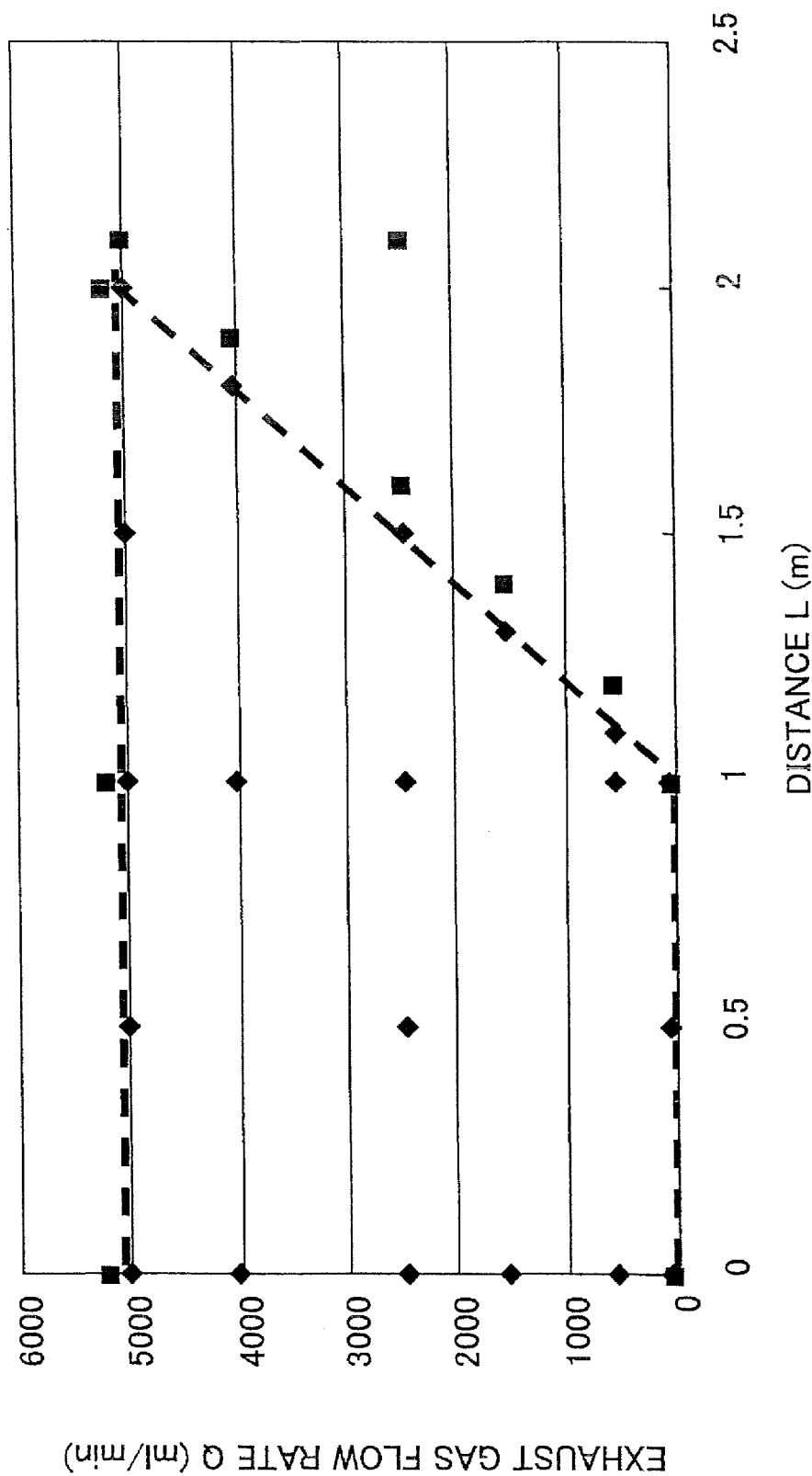
FIG. 12 is a diagram showing a preferable construction of the exhaust gas purifying apparatus of the embodiment of the present invention.

FIG. 12 is a graph showing the area in which the mass of the particulate matter deposited in the primary diesel particulate filter (DPF) 22 can be evaluated accurately within the error of about ±10% wherein FIG. 12 represents the area as a function of the flow rate Q [ml/min] of the exhaust gas flowing through the secondary exhaust line 21A and a distance L, wherein the distance L is defined in the embodiment of FIG. 6 and represents the distance to the secondary diesel particulate filter 22A from the point in which the secondary exhaust line 21A has branched from the primary exhaust line 21.

Table 1 below summarizes the experiments of FIG. 12.

TABLE 1

|  | Outer dimension | Wall thickness | Cell density | porosity | Average pore diameter |
|---|---|---|---|---|---|
| Secondary DPF 22A | 2 mm × 2 mm × 50 mm | 0.4 mm | — | 42% | 11 μm |
| Primary DPF 22 | Ø143.8 mm × 150 mm | 0.4 mm | 200 cpsi | 42% | 11 μm |

Referring to Table 1, the experiment of FIG. 12 was conducted by providing the exhaust gas purifying apparatus of the embodiment of FIG. 6 to the exhaust line of a two-litter diesel engine and operating the diesel engine at the condition of 3000 rpm/50N for 5 hours. In the experiment, the deposition amount of the particulate matter in the primary diesel particulate filter (DPF) 22 is obtained. With this experiment, the exhaust gas was emitted to the exhaust line 21 with a flow rate of about 350 m³/h.

With the experiment of FIG. 12, an SiC component of the outer dimension of 2 mm×2 mm×50 mm, the wall thickness of 0.4 mm, the porosity of 42% and the average pore diameter of 11 μm, has been used for the secondary diesel particulate filter 22A. Further, for the primary diesel particulate filter (DPF) 22, an SiC component of the diameter of 143.8 mm and the height of 150 mm, the wall thickness of 0.4 mm, the porosity of 42%, the average pore diameter of 11 μm was used, wherein the SiC component used for the primary diesel particulate filter (DPF) 22 included therein the cells with a density of 200 cpsi (cells per square inch). In the experiment, the error between the amount of the particulate matter actually deposited on the primary diesel particulate filter (DPF) 22 and the amount of the particulate matter in the primary diesel particulate filter (DPF) 22 as evaluated from the differential pressure of the secondary diesel particulate filter 22A was obtained while changing the distance to the secondary diesel particulate filter from the branching point of the secondary exhaust line 21A from the exhaust line 21 variously. Here, it should be noted that the amount of the particulate matter actually deposited in the primary diesel particulate filter (DPF) 22 is obtained directly by measuring the weight of the filter 22.

Further, with the experiment of FIG. 12, the diameter of the exhaust line 21 is set to 10 mm, while the diameter of the secondary exhaust line 21A is set to 150 mm. Further, the flow rate of the exhaust gas in the secondary exhaust line 21A is changed in the range of 0 to 5000 ml/min. Further, the regeneration of the secondary particulate filter 22A is carried out each time the particulate matter is deposited to the filter 22A with the amount of 0.5 g/l.

Table 2 below summarizes the experimental result.

TABLE 2

|  | flow rate (ml/min) | Distance (m) | Precision of evaluation (%) |
|---|---|---|---|
| Example 1 | 50 | 0 | 2.1 |
| Example 2 | 50 | 0.5 | 4.2 |
| Example 3 | 50 | 1.0 | 8.3 |
| Example 4 | 545 | 0 | 3.5 |
| Example 5 | 545 | 1.0 | 7.5 |
| Example 6 | 545 | 1.1 | 7.8 |
| Example 7 | 1535 | 0 | 5.4 |
| Example 8 | 1535 | 1.3 | 8.1 |
| Example 9 | 2475 | 0 | 5.8 |
| Example 10 | 2475 | 0.5 | 4.3 |
| Example 11 | 2475 | 1.0 | 5.8 |
| Example 12 | 2475 | 1.5 | 7.6 |
| Example 13 | 4010 | 0 | 7.2 |
| Example 14 | 4010 | 1.0 | 5.6 |
| Example 15 | 4010 | 1.8 | 8.4 |
| Example 16 | 5000 | 0 | 8.6 |
| Example 17 | 5000 | 0.5 | 7.1 |
| Example 18 | 5000 | 1.0 | 6.2 |
| Example 19 | 5000 | 1.5 | 8.2 |
| Example 20 | 5000 | 2.0 | 8.6 |
| Comparison 1 | 5000 | 2.1 | 12.3 |
| Comparison 2 | 2475 | 2.1 | 15.4 |
| Comparison 3 | 30 | 0 | 12.4 |
| Comparison 4 | 30 | 1.0 | 14.7 |
| Comparison 5 | 545 | 1.2 | 11.5 |
| Comparison 6 | 1535 | 1.4 | 12.3 |
| Comparison 7 | 2475 | 1.6 | 11.9 |
| Comparison 8 | 4010 | 1.9 | 12.1 |
| Comparison 9 | 5200 | 0 | 14.3 |
| Comparison 10 | 5200 | 1.0 | 12.7 |
| Comparison 11 | 5200 | 2.0 | 11.4 |

Referring to Table 2, it can be seen that there exists a tendency that the error in the estimated deposition amount of the particulate patter in the primary diesel particulate filter (DPF) 22 as obtained by using the secondary diesel particulate filter 22A decreases generally with decreasing distance to the secondary diesel particulate filter 22A from the foregoing branching point and that the error decreases with increasing flow rate of the exhaust gas in the secondary diesel particulate filter 22A.

FIG. 12 is a graph showing the result of Table 2 above, wherein ♦ represents the data point where the error is 10% or less, while ■ represents the data point where the error exceeds 10%. Further, the broken line represents the boundary between the data points ♦ and the data points ■.

Referring to FIG. 12, it can be seen that there is imposed a limitation in the flow rate Q of the exhaust gas in the secondary exhaust line 21A in order to evaluate the deposition amount of the particulate matter in the primary diesel particulate filter (DPF) 22 within the error of ±10% from the differential pressure value of the secondary diesel particulate filter 22A. Thus, it is not possible to achieve precise evaluation when this flow rate Q is too small or too large. More specifically, a precise evaluation of the deposition amount becomes possible in the case the distance L is about 1 m or less and the flow rate Q of the exhaust gas is about 50 ml/min or more and about 5000 ml/minute or less. Further, in the case the distance L is about 1 m or more and about 2 m or less, the precise evaluation of the deposition amount becomes possible when the flow rate Q of the exhaust gas satisfies the relationship: 4950L-4900≦Q≦about 5000.

Thus, with increasing distance L, the range of the flow rate in which precise evaluation of the deposition amount is possible is narrowed.

Thus, the foregoing results indicate that it is preferable to design the exhaust gas purifying apparatus of the embodiment of FIG. 6 such that the foregoing relationship is satisfied and the operational point falls within the region defined in FIG. 12 by the broken lines. Particularly, it can be seen that the distance L is set preferably to about 2 m or less. When the distance L exceeds about 2 m, it is no longer possible to evaluate the deposition amount of the particulate matter in the primary diesel particulate filter (DPF) 22 within the error of about 10%, even when the flow rate of the exhaust gas is increased.

Further, it will be noted from the relationship of FIG. 12 that the evaluation within the error of about 10% becomes no longer possible when the flow rate of the exhaust gas in the secondary diesel particulate filter 22A has exceeded the value of about 5000 ml/min. When the flow rate of the exhaust gas in the secondary diesel particulate filter 22A exceeds the value of about 5000 ml/min, there is a need of frequent regeneration of the secondary diesel particulate filter 22A.

Further, while the explanation heretofore has been made for the case of using a honeycomb component of SiC for the primary diesel particulate filter (DPF) 22 and the secondary diesel particulate filter 22A, the embodiment of the present invention is by no means limited to such particular filter components, and it is also possible to use Si—SiC, a nitride such as aluminum nitride, silicon nitride, boron nitride, tungsten nitride, or the like, a carbide such as Zirconium carbide, titanium carbide, tantalum carbide, tungsten carbide, or the like, an oxide such as alumina, zirconium oxide, cordierite, mullite, silica, aluminum titanate, or a porous body of metal such as stainless steel. Further, it is possible to use a structural body such as corrugate or element plate in addition to the honeycomb structure.

The exhaust gas purifying apparatus of the embodiment of the present invention has a compact size and is applicable not only to large vehicles such as trucks or industrial machines but also to passenger cars. Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An exhaust gas purifying apparatus, comprising:
   a primary diesel particulate filter provided in a primary exhaust line of a diesel engine;
   a secondary exhaust line branched from said primary exhaust line from an upstream side of said primary diesel particulate filter, said secondary exhaust line branching a flow of an exhaust gas from said diesel engine;
   a secondary diesel particulate filter provided in said secondary exhaust line, said secondary diesel particulate filter having a soot storage capacity smaller than the soot storage capacity of said primary diesel particulate filter; and
   a differential pressure measuring part measuring a differential pressure between an inlet and an outlet of said secondary diesel particulate filter, wherein a distance to said secondary diesel particulate filter from a branching point of said secondary exhaust line from said primary exhaust line is about 2 m or less.

2. The exhaust gas purifying apparatus as claimed in claim 1, wherein an exhaust gas is caused flow through said secondary exhaust line with a flow rate of about 5000 ml/min or less.

3. The exhaust gas purifying apparatus as claimed in claim 1, wherein an exhaust gas is caused flow through said secondary exhaust line with a flow rate of about 5000 ml/min or less and wherein said distance is about 1 m or less.

4. The exhaust gas purifying apparatus as claimed in claim 1, wherein said secondary exhaust line includes a flow meter.

5. The exhaust gas purifying apparatus as claimed in claim 1, wherein said secondary diesel particulate filter includes a temperature measuring part.

6. The exhaust gas purifying apparatus as claimed in claim 1, wherein said secondary diesel particulate filter includes a heater.

7. The exhaust gas purifying apparatus as claimed in claim 1, further including a valve for maintaining a flow rate of an exhaust gas in said secondary exhaust line at a predetermined value.

8. The exhaust gas purifying apparatus as claimed in claim 1, further including a holder, and wherein at least one of said differential pressure measuring part, said temperature measuring part, said secondary diesel particulate filter, and said flow meter is accommodated in said holder.

9. An exhaust gas purifying apparatus, comprising:
a primary diesel particulate filter provided in a primary exhaust line of a diesel engine;
a secondary exhaust line branched from said primary exhaust line from an upstream side of said primary diesel particulate filter;
a secondary diesel particulate filter provided in said secondary exhaust line, said secondary diesel particulate filter having a soot storage capacity smaller than the soot storage capacity of said primary diesel particulate filter; and
a differential pressure measuring part measuring a differential pressure between an inlet and an outlet of said secondary diesel particulate filter,
wherein a distance L [m] to said secondary diesel particulate filter from a branching point of said secondary exhaust line from said primary exhaust line is set so as to satisfy the relationship
about $50 \leqq Q \leqq$ about $5000$ ($0 \leqq L \leqq$ about $1$)
$4950L - 4900 \leqq Q \leqq$ about $5000$ (about $1 \leqq L \leqq$ about $2$)
where Q [ml/min] represents a flow rate of said exhaust gas in said secondary exhaust line.

10. The exhaust gas purifying apparatus as claimed in claim 9, wherein said secondary exhaust line includes a flow meter or an equivalent meter.

11. The exhaust gas purifying apparatus as claimed in claim 9, wherein said secondary diesel particulate filter includes a temperature measuring part.

12. The exhaust gas purifying apparatus as claimed in claim 9, wherein said secondary diesel particulate filter includes a heater.

13. The exhaust gas purifying apparatus as claimed in claim 9, further including a valve for maintaining a flow rate of an exhaust gas in said secondary exhaust line at a predetermined value.

14. The exhaust gas purifying apparatus as claimed in claim 9, further including a holder, and wherein at least one of said differential pressure measuring part, said temperature measuring part, said secondary diesel particulate filter, and said flow meter is accommodated in said holder.

* * * * *